United States Patent
Johs et al.

(10) Patent No.: US 7,075,650 B1
(45) Date of Patent: Jul. 11, 2006

(54) DISCRETE POLARIZATION STATE SPECTROSCOPIC ELLIPSOMETER SYSTEM AND METHOD OF USE

(75) Inventors: Blaine D. Johs, Lincoln, NE (US); Martin M. Liphardt, Lincoln, NE (US); Ping He, Lincoln, NE (US); Jeffrey S. Hale, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 449 days.

(21) Appl. No.: 10/613,118

(22) Filed: Jul. 7, 2003

Related U.S. Application Data

(63) Continuation-in-part of application No. 09/945,962, filed on Sep. 4, 2001, now abandoned, and a continuation-in-part of application No. 09/517,125, filed on Feb. 29, 2000, now abandoned, and a continuation-in-part of application No. 09/246,888, filed on Feb. 8, 1999, now Pat. No. 6,084,675, and a continuation-in-part of application No. 09/232,257, filed on Jan. 19, 1999, now Pat. No. 6,141,102, and a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/225,076, filed on Jan. 4, 1999, now Pat. No. 5,963,325, and a continuation-in-part of application No. 09/225,371, filed on Jan. 4, 1999, now Pat. No. 6,100,981, which is a continuation-in-part of application No. 08/997,311, filed on Dec. 23, 1997, now Pat. No. 5,946,098, which is a continuation-in-part of application No. 08/912,211, filed on Aug. 15, 1997, now Pat. No. 5,872,630, and a continuation-in-part of application No. 08/618,820, filed on Mar. 20, 1996, now Pat. No. 5,706,212, which is a continuation-in-part of application No. 08/530,892, filed on Sep. 20, 1995, now Pat. No. 5,666,201.

(60) Provisional application No. 60/438,187, filed on Jan. 7, 2003, provisional application No. 60/229,755, filed on Sep. 5, 2000.

(51) Int. Cl.
*G01J 4/00* (2006.01)

(52) U.S. Cl. ...................................... 356/369
(58) Field of Classification Search ........ 356/364–369; 250/225
See application file for complete search history.

(56) References Cited

U.S. PATENT DOCUMENTS

| | | | |
|---|---|---|---|
| 3,947,688 A | 3/1976 | Massey | 250/495 |
| 4,053,232 A | 10/1977 | Dill et al. | 356/118 |
| 4,647,207 A | 3/1987 | Bjork et al. | 356/369 |
| 4,826,321 A | 5/1989 | Coates et al. | 356/351 |
| 4,982,206 A | 1/1991 | Kessler et al. | 346/108 |

(Continued)

FOREIGN PATENT DOCUMENTS

SU 1518728 10/1989

*Primary Examiner*—Hoa Q. Pham
(74) *Attorney, Agent, or Firm*—James D. Welch

(57) ABSTRACT

A spectroscopic ellipsometer system comprising a plurality of individual sources which are sequentially energized to provide a sequence of beams, each of different polarization state but directed along a common locus toward a sample. The prefered spectroscopic ellipsometer system has no parts which move during data collection, and it provides a progressive plurality of sequentially discrete, rather than continuously varying, polarization states.

28 Claims, 13 Drawing Sheets

U.S. PATENT DOCUMENTS

| | | | |
|---|---|---|---|
| 5,155,623 A | 10/1992 | Miller et al. | 359/495 |
| 5,179,462 A | 1/1993 | Kageyama et al. | 359/204 |
| 5,329,357 A | 7/1994 | Bernoux et al. | 356/369 |
| 5,373,359 A | 12/1994 | Woollam et al. | 356/328 |
| 5,581,350 A | 12/1996 | Chen et al. | 356/369 |
| 5,666,201 A * | 9/1997 | Johs et al. | 356/369 |
| 5,706,212 A * | 1/1998 | Thompson et al. | 702/85 |
| 5,757,494 A | 5/1998 | Green et al. | 356/369 |
| 5,872,630 A | 2/1999 | Johs et al. | 356/369 |
| 5,946,098 A * | 8/1999 | Johs et al. | 356/364 |
| 5,956,145 A | 9/1999 | Green et al. | 356/364 |
| 5,963,325 A * | 10/1999 | Johs et al. | 356/364 |
| 5,963,327 A | 10/1999 | He et al. | 356/369 |
| 6,084,674 A * | 7/2000 | Johs et al. | 356/364 |
| 6,084,675 A * | 7/2000 | Herzinger et al. | 356/369 |
| 6,100,981 A * | 8/2000 | Johs et al. | 356/364 |
| 6,118,537 A * | 9/2000 | Johs et al. | 356/369 |
| 6,141,102 A * | 10/2000 | Johs et al. | 356/364 |
| 6,268,917 B1 | 7/2001 | Johs | 356/369 |

* cited by examiner

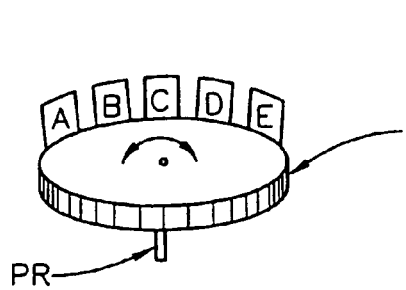
FIG. 3a
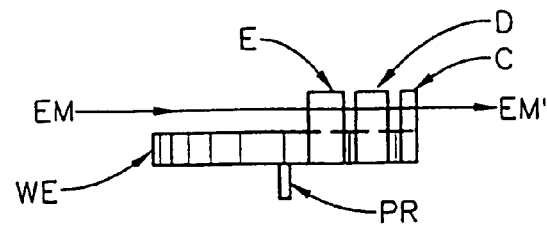
FIG. 3b
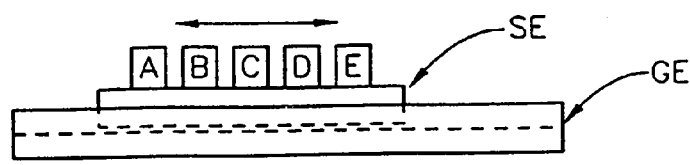
FIG. 3c
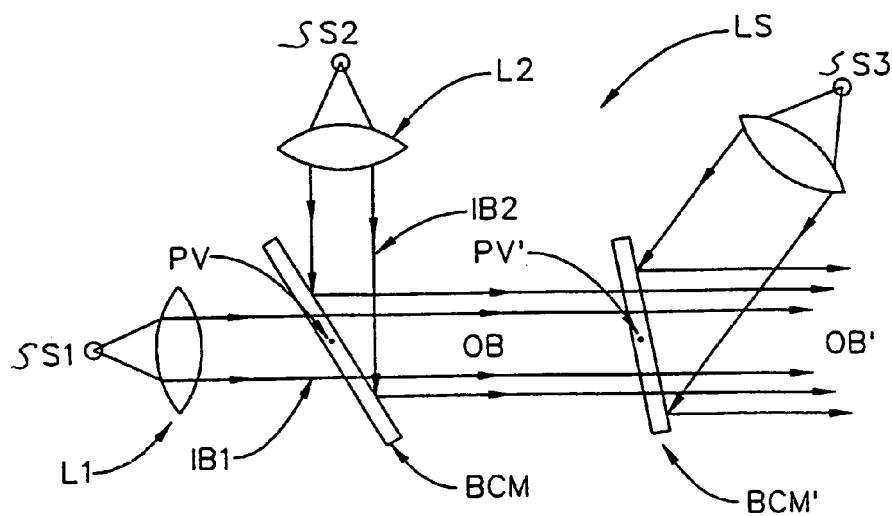
FIG. 3d1

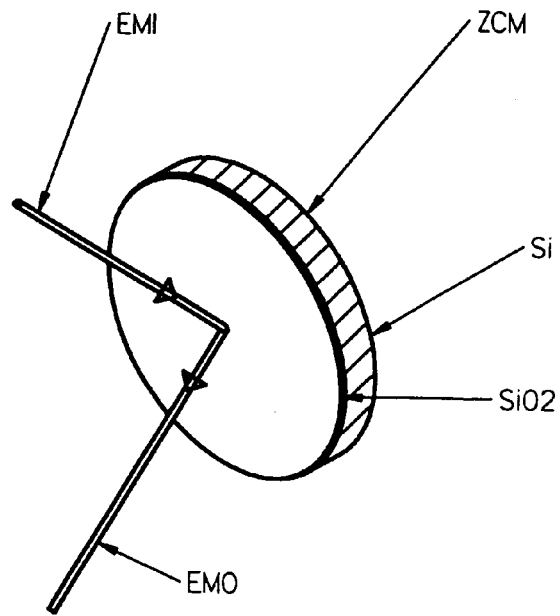
FIG. 3d2
Spectrum of SE with and without 1200Å SiO2/Si Mirror
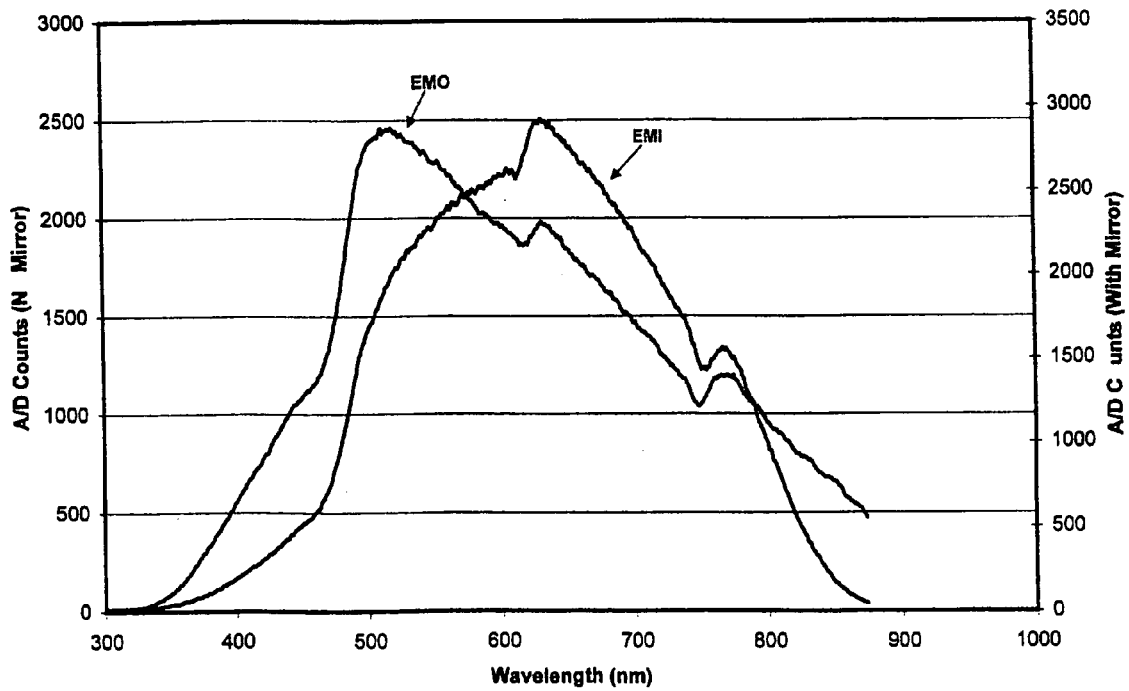
FIG. 3d3

Providing a sample system investigation system comprising:
- a) a plurality of electromagnetic radiation s urces, each thereof optionally having polarization state setting means functionally associated therewith;
- b) a means for accepting at least two electromagnetic beams which approach along different loci, and providing an electromagnetic beam which exits therefrom along a single locus;
- c) a stage for supporting a sample system;
- d) at least one detector system;
- e) computation means;

said at least first means for accepting at least two electromagnetic beams which approach along different loci, and providing an electromagnetic beam which exits therefrom along a single locus, being positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system; said at least one detector system being positioned to intercept a beam which emerges from the sample system on said stage for supporting a sample system after said beam interacts therewith.

---

Sequentially energizing at least two of said sources of electromagnetic radiation and accumulating data from said at least one detector system.

---

Providing a mathematical model of the sample system and by simultaneous mathematical regression onto said data sets, evaluating parameters in said mathematical model.

FIG. 4a

Providing a spectroscopic ellipsometer system comprising:
- a) a plurality of electromagnetic radiation sources, each thereof optionally having polarization state setting means functionally associated therewith;
- b) a means for accepting at least two electromagnetic beams which approach along different loci, and providing an electromagnetic beam which exits therefrom along a single locus;
- c) a stage for supporting a sample system;
- d) at least one detector system;
- e) computation means;

said at least first means for accepting at least two electromagnetic beams which approach along different loci, and providing an electromagnetic beam which exits therefrom along a single locus, being positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system; said at least one detector system being positioned to intercept a beam which emerges from the sample system on said stage for supporting a sample system after said beam interacts therewith.

---

For each of at least two ellipsometrically distinguished sample systems, obtaining at least one multi-dimensional data set comprising intensity as a function of wavelength and as a function of a plurality of polarization states of a beam of electromagnetic radiation sequentially provided by said plurality of sources of polychromatic electromagnetic radiation.

---

Providing a mathematical model of the ellipsometer system, including provision for accounting for the polarization state of a beam of electromagnetic radiation provided by said sources of polychromatic electromagnetic radiation utilized.

---

By simultaneous mathematical regression onto said data sets, evaluating parameters in said mathematical model.

FIG. 4b

DISCRETE POLARIZATION STATE SPECTROSCOPIC ELLIPSOMETER SYSTEM AND METHOD OF USE

This Application is also a Continuation-in-Part of application Ser. No. 09/945,962 Filed Sep. 4, 2001, now abandoned and therevia of applications: Ser. No. 09/517,125 Filed Feb. 29, 2000; now abandoned; and of Ser. No. 09/246,888 filed Feb. 8, 1999, (now U.S. Pat. No. 6,084,675); and further of: Ser. No. 09/225,118 filed Jan. 4, 1999 filed Jan. 4, 1999 (now U.S. Pat. No. 6,084,674); Ser. No. 09/223,822 filed Jan. 4, 1999, (now U.S. Pat. No. 6,118,537); Ser. No. 09/232,257 filed Jan. 19, 1999, (now U.S. Pat. No. 6,141,102); Ser. No. 09/225,371 filed Jan. 4, 1999, (now U.S. Pat. No. 6,100,981); Ser. No. 09/225,076 filed Jan. 4, 1999, (now U.S. Pat. No. 5,963,325) which Applications depended from Ser. No. 08/997,311 filed Dec. 23, 1997, (now U.S. Pat. No. 5,946,098). Further, via the Ser. No. 09/246,888 Application, this application is a Continuation-In-Part of: Ser. No. 08/912,211 filed Aug. 15, 1997, (now U.S. Pat. No. 5,872,630), which Continued-In-Part from Ser. No. 08/530,892 filed Sep. 20, 1995, (now U.S. Pat. No. 5,666,201); and and is also a CIP of Ser. No. 08/618,820 filed Mar. 20, 1996, (now U.S. Pat. No. 5,706,212). In addition, priority is claimed from: Ser. No. 09/162,217 filed Sep. 29, 1998 via above Applications. This Application also Claims benefit of Provisional Application Ser. No. 60/229,755 filed Sep. 5, 2000 in addition to, via the 962 Application, Provisional Application Ser. Nos. 60/229,755 Filed Sep. 5, 2000, and Ser. No. 60/438,187 Filed Jan. 7, 2003.

TECHNICAL FIELD

The present invention relates to ellipsometer systems, as well as methods of calibration and use thereof. More particularly the present invention is, in its prefered embodiment, a spectroscopic ellipsometer system comprising a plurality of individual sources which are sequentially energized to provide a sequence of beams, each thereof being of a different polarization state, but directed along a common locus toward a sample. The preferred spectroscopic ellipsometer of the present invention system has no parts which move during data collection and provides a progressive plurality of sequentially discrete, rather than continuously varying, polarization states.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

In general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$$PSI = |r_p/r_s|; \text{ and}$$

$$DELTA = (\Delta r_p - \Delta r_s).$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. As described elsewhere in this Specification, the present invention breaks with this convention and provides that no element be continuously rotated during data acquisition but rather that a sequence of discrete polarization states be imposed during data acquisition. This approach allows eliminating many costly components from conventional rotating element ellipsometer systems, and, hence, production of an "Ultra-Low-Cost" ellipsometer system. It is noted, that nulling ellipsometers also exist in which elements therein are rotatable in use, rather than rotating. Generally, use of a nulling ellipsometer system involves imposing a linear polarization state on a beam of electromagnetic radiation with a polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

It is further noted that reflectometer systems are generally sequentially comprised of:
a. a Source of a beam electromagnetic radiation;
d. (optional additional element(s));
e. a sample system;
f. (optional additional element(s));
i. a Spectroscopic Detector System;

and that reflectometer systems monitor changes in intensity of a beam of electromagnetic radiation caused to interact with a sample system. That is, the ratio of, and phase angle between, orthogonal components in a polarized beam are not of direct concern.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patents of which the Inventor is aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems.

U.S. Pat. No. 6,268,917 to Johs discloses a system for combining a plurality of polychromatic beams into a single beam which has a smoother intensity vs. wavelength plot.

Further Patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are No. RE 34,783, U.S. Pat. Nos. 4,373,817, and 5,045,704 to Coates; and U.S. Pat. No. 5,452,091 to Johnson.

A Patent to Bjork et al., U.S. Pat. No. 4,647,207 is disclosed as it describes an ellipsometer system which has provision for sequentially positioning a plurality of reflective polarization state modifiers in a beam of electromagnetic radiation. While said 207 Patent mentions investigating a sample system in a transmission mode, no mention or suggestion is found for utilizing a plurality of transmitting polarization state modifiers, emphasis added. U.S. Pat. Nos. 4,210,401; 4,332,476 and 4,355,903 are also identified as being cited in the 207 Patent. It is noted that systems as disclosed in these Patents, (particularly in the 476 Patent), which utilize reflection from an element to modify a polarization state can, if such an element is an essential duplicate of an investigated sample and is rotated ninety degrees therefrom, the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

A Patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other Patents identified in a Search which identified said 918 Patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other Patents are not believed to be particularly relevant, however.

A Patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

As present invention preferred practice is to utilize a spectroscopic source of electromagnetic radiation with a relatively flat spectrum over a large range of wavelengths Patent No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 Patent. Another Patent, U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively. Another Patent, U.S. Pat. No. 3,947,688 to Massey, describes a method of generating tuneable coherent ultraviolet light, comprising use of an electromagnetic electromagnetic beam combining system. A Patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A Patent to Wright, U.S. Pat. No. 5,002,371 is also mentioned as describing a beam splitter system which operates to separate "P" and "S" orthogonal components in a beam of polarized electromagnetic radiation. Another Patent, U.S. Pat. No. 6,384,916 to Furtak is disclosed as it describes a parallel detecting spectroscopic ellipsometer having no moving parts.

In addition to the identified Patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

Another paper, by Gottesfeld et al., titled "Combined Ellipsometer and Reflectometer Measurements of Surface Processes on Nobel Metals Electrodes", Surface Sci., 56 (1976), is also identified as describing the benefits of combining ellipsometry and reflectometry.

A paper by Smith, titled "An Automated Scanning Ellipsometer", Surface Science, Vol. 56, No. 1. (1976), is also mentioned as it describes an ellipsometer system which does not require any moving, (eg. rotating), elements during data acquisition.

Four additional papers by Azzam and Azzam et al. are also identified and are titled:
"Multichannel Polarization State Detectors For Time-Resolved Ellipsometry", Thin Solid Film, 234 (1993); and
"Spectrophotopolarimeter Based On Multiple Reflections In A Coated Dielectric Slab", Thin Solid Films 313 (1998); and
"General Analysis And Optimization Of The Four-Detector Photopolarimeter", J. Opt. Soc. Am., A, Vol. 5, No. 5 (May 1988); and
"Accurate Calibration Of Four-Detector Photopolarimeter With Imperfect Polarization Optical Elements", J. Opt. Soc. Am., Vol. 6, No. 10, (October 1989);

as they describe alternative approaches concerning the goal of the present invention.

Even in view of relevant prior art, there remains need for a low cost spectroscopic ellipsometer system which:
  has no moving parts during data acquisition;
  utilizes a plurality of separate source means to effect a plurality of sequential discrete, rather than continuously varying, polarization states during said data acquisition; and
  optionally comprises a beam splitting analyzer, and multiple detector systems.

In addition there remains need for:

a calibration procedure for said spectroscopic ellipsometer system which involves the gathering of spectroscopic data at a plurality of discrete polarization states for each of some number of sample systems; and a method for applying ths disclosed system in sample investigation.

The present invention responds to said identified needs.

DISCLOSURE OF THE INVENTION

The prefered embodiment of the disclosed invention is a low cost sample system investigation system comprising:
  a) a plurality of electromagnetic radiation sources, each thereof optionally having polarization state setting means functionally associated therewith;
  b) a means for accepting at least two electromagnetic beams which approach along different loci, and providing an electromagnetic beam which exits therefrom along a single locus;
  c) a stage for supporting a sample system; and
  d) at least one detector system.

Said at least first means for accepting at least two electromagnetic beams which approach along different loci, and providing an electromagnetic beam which exits therefrom along a single locus, is positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system.

Said at least one detector system is positioned to intercept a beam which emerges from the sample system on said stage for supporting a sample system after said beam of electromagnetic radiation interacts therewith.

While not a requirement, the prefered arrangement provides that the sample system investigation system each of the plurality of electromagnetic radiation sources has polarization state setting means functionally associated therewith. Said polarization state setting means associated with said first electromagnetic radiation source is set to provide a different polarization state on a beam of electromagnetic radiation emerging therefrom than does the polarization state setting means associated with said second electromagnetic radiation source impose on a beam of electromagnetic radiation emerging from said second electromagnetic radiation source. While all of the plurality of electromagnetic radiation sources can be selected to provide a beam of polychromatic electromagnetic radiation, at least one source can provide substantially monochromatic electromagnetic radiation, and it is noted that where different sources of the plurality of electromagnetic radiation sources provide different wavelengths, that alone can distinguish the sources without need for the optional different polarization states being effected.

With the system described, it should be appreciate that a method of analyzing a sample system comprising the steps of:

A) providing a sample system investigation system comprising:
   a) a plurality of electromagnetic radiation sources, each thereof optionally having polarization state setting means functionally associated therewith;
   b) a means for accepting at least two electromagnetic beams which approach along different loci, and providing an electromagnetic beam which exits therefrom along a single locus;
   c) a stage for supporting a sample system;
   d) at least one detector system;
   e) computation means;

said at least first means for accepting at least two electromagnetic beams which approach along different loci, and providing an electromagnetic beam which exits therefrom along a single locus, being positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system;

said at least one detector system being positioned to intercept a beam which emerges from the sample system on said stage for supporting a sample system after said beam interacts therewith;

B) energizing one of said sources of electromagnetic radiation and accumulating data from said at least one detector system;

C) optionally energizing a second of said sources of electromagnetic radiation and accumulating data from said at least one detector system;

D) optionally energizing a third of said sources of electromagnetic radiation and accumulating data from said at least one detector system;

E) optionally energizing a fourth of said sources of electromagnetic radiation and accumulating data from said at least one detector system;

F) applying said computation means to analyze said sample system utilizing said accumulated data.

Said method, in the step of providing a sample system investigation system can involve providing a sample system investigation system characterized by a selection from the group consisting of:
   none of said plurality of electromagnetic radiation sources has polarization state setting means functionally associated therewith;
   at least one of said plurality of electromagnetic radiation sources has polarization state setting means functionally associated therewith;
   at least one of said plurality of electromagnetic radiation sources provides a beam of substantially monochromatic electomagnetic radiation;
   at least one of said plurality of electromagnetic radiation sources provides a beam of polychromatic electomagnetic radiation;
   at least a first and a second of said plurality of electromagnetic radiation sources each have polarization state setting means functionally associated therewith, the polarization state setting means functionally associated with said first electromagnetic radiation source being set to provide a different polarization state to a beam of electromagnetic radiation emerging therefrom than does the polarization state setting means functionally associated with said second electromagnetic radiation source impose on a beam of electromagnetic radiation emerging from said second electromagnetic radiation source.

Where said method provides that at least a first and a second of said plurality of electromagnetic radiation sources each have polarization state setting means functionally associated therewith, the polarization state setting means associated with said first electromagnetic radiation source being set to provide a different polarization state on a beam of electromagnetic radiation emerging therefrom than does the polarization state setting means associated with said second electromagnetic radiation source impose on a beam of electromagnetic radiation emerging from said second electromagnetic radiation source, and in which said at least first and second of said plurality of electromagnetic radiation sources are sequentially energized in steps B) and (C).

The prefered embodiment of the disclosed sample system investigation system can comprise:
   a) at least a first and a second source of electromagnetic radiation, each thereof having polarization state setting means functionally associated therewith;
   b) at least a first electromagnetic beam combining means;
   c) a stage for supporting a sample system;
   d) analyzer means; and
   e) at least one detector system.

Said at least a first electromagnetic beam combining means is positioned with respect to first and second sources of electromagnetic radiation such that a polarized beam of electromagnetic radiation from said first source of electromagnetic radiation, when it is energized, passes through said at least a first electromagnetic beam combining means, and such that a polarized beam of electromagnetic radiation from said second source of electromagnetic radiation, when it is energized, reflects from said at least a first electromagnetic beam combining means such that a beam of electromagnetic radiation exiting said first electromagnetic beam combining means proceeds along a locus which is directed toward a sample system placed on said stage for supporting a sample system.

Said at least one detector system comprising said analyzer means and being positioned to intercept a beam which emerges from the sample system on said stage for supporting a sample system after interaction therewith.

Said sample system investigation system can further comprsise:
   f) a third and a fourth source of electromagnetic radiation, each thereof having polarization state setting means functionally associated therewith;
   g) a second electromagnetic beam combining means; and
   h) a third electromagnetic beam combining means.

Said third electromagnetic beam combining means is positioned such that said beam of electromagnetic beam exiting said first electromagnetic beam combining means along a locus which is directed toward a sample system placed on said stage for supporting a sample system, passes therethrough before proceeding toward said sample system. Said second electromagnetic beam combining means is positioned with respect to said third and fourth sources of electromagnetic radiation such that a polarized beam of electromagnetic radiation from said third source of electromagnetic radiation, when it is energized, passes through said second electromagnetic beam combining means, and such that a polarized beam of electromagnetic radiation from said fourth source of electromagnetic radiation, when it is energized, reflects from said second electromagnetic beam combining means. In use, a beam of electromagnetic radiation exiting said second electromagnetic beam combining means along a locus which is directed toward said third electromagnetic beam combining means, reflects off thereof and proceed toward said sample system Said at least one detector system which comprises analyzer means, is positioned to intercept a beam which emerges from the sample system on said stage for supporting a sample system after interaction therewith.

Said sample system investigation system preferably provides that the polarization state setting means functionally associated with said first and second sources of electromagnetic radiation are at azimuthal orientations offset from one another, and that said azimuthal settings are offset from the third and fourth sources of electromagnetic radiation, which are at azimuthal orientations offset from one another. Preferably the azimuthal offsets, first to second, second to third, and third to fourth polarization state setting means are at azimuthal orientations which are offset 45 degrees from one another.

The prefered sources of electromagnetic radiation comprise light emitting diodes, and said first, second, third and fourth sources of electromagnetic radiation can variously comprise light emitting diodes which emit various colors, or a white spectrum.

The sample system investigation system contains a Detector, typically preceded by a Rotatable Analyzer which is set, and remains stationary, during data acquisition.

A prefered sample system investigation system contains a polarization state dependent beam splitter and two detectors, each of which receive a different beam emerging from said beam splitter.

A disclosed invention method of analyzing a sample system comprises the steps of:

A) providing a sample system investigation system comprising:
 a) at least a first and a second source of electromagnetic radiation, each thereof having polarization state setting means functionally associated therewith, said polarization state setting means functionally associated with said first and said second sources of electromagnetic radiation being at azimuthal orientations offset from one another;
 b) first electromagnetic beam combining means;
 c) a stage for supporting a sample system;
 d) analyzer means;
 e) at least one detector system;
 f) computational means.

as described above; then in either order practicing the following steps:

B) energizing said first source of electromagnetic radiation and accumulating data from said at least one detector system; and C) energizing said second source of electromagnetic radiation and accumulating data from said at least one detector system;

F) applying said computation means to analyze said sample system utilizing said accumulated data.

Another recitation of a disclosed invention method of analyzing a sample system comprising the steps of:

A) providing a sample system investigation system comprising:
 a) first, second, third and fourth sources of electromagnetic radiation, each thereof having polarization state setting means functionally associated therewith, said polarization state setting means functionally associated with said first, second, third and fourth sources of electromagnetic radiation being at orientations offset from one another;
 b) first, second and third electromagnetic beam combining means;
 c) a stage for supporting a sample system;
 d) analyzer means;
 e) at least one detector system;
 f) a computation means.

Said first, second, third and forth sources of electromagnetic radiation and said first, second and third beam combining means being oriented as described above, and said at least one detector system which comprises said analyzer means also being positioned to intercept a beam which emerges from the sample system, as described above. Said method then involves, in any functional order practicing at least two steps selected from the group consisting of:

B) energizing said first source of electromagnetic radiation and accumulating data from said at least one detector system;

C) energizing said second source of electromagnetic radiation and accumulating data from said at least one detector system;

D) energizing said third source of electromagnetic radiation and accumulating data from said at least one detector system;

E) energizing said fourth source of electromagnetic radiation and accumulating data from said at least one detector system; and F) applying said computation means to analyze said sample system utilizing said accumulated data.

The sample system investigation system can further comprise at least one compensator prior to and/or after the stage for supporting a sample system.

As the disclosed invention is a low cost spectroscopic ellipsometer system, additional low cost spectroscopic ellipsometer systems which also provide a sequence of descrete polariation states are also described herein for contrast and comparison. Such an alternative low cost spectroscopic ellipsometer system, (which has parts which move during data acquisition), comprises:
 a source of polychromatic electromagnetic radiation;
 a polarizer which is fixed in position during data acquisition;
 a stage for supporting a sample system;
 an analyzer which is fixed in position during data acquisition; and
 a multi-element spectroscopic detector system.

In addition, said ellipsometer system further comprises at least one means for discretely, sequentially, modifying a polarization state of a beam of electromagnetic radiation through a plurality of polarization states. The at least one means for discretely, sequentially, modifying a polarization state of a beam of electromagnetic radiation through a plurality of polarization states, is positioned between said polarizer and said stage for supporting a sample system, and/or and between said stage for supporting a sample system and said analyzer, and so that said beam of electromagnetic radiation transmits through a polarization state modifier element thereof in use.

Said alternative low cost spectroscopic ellipsometer system can also comprise a combination spectroscopic reflectometer/ellipsometer system basically comprising:
- a source of polychromatic electromagnetic radiation;
- a stage for supporting a sample system;
- a multi-element spectroscopic detector system.

The combination spectroscopic reflectometer/ellipsometer system further comprises, in the ellipsometer system portion thereof, a polarizer, (which is fixed in position during data acquisition), present between the source of polychromatic electromagnetic radiation and the stage for supporting a sample system, and an analyzer, (which is fixed in position during data acquisition), present between the stage for supporting a sample system and the multi-element spectroscopic detector system. The ellipsometer system also comprises at least one means for discretely, sequentially, modifying a polarization state of a beam of electromagnetic radiation through a plurality of polarization states present between said polarizer and said stage for supporting a sample system, and/or between said stage for supporting a sample system and said analyzer, and positioned so that said beam of electromagnetic radiation transmits through a polarization state modifier element therein during use.

Additionally, the combination spectroscopic reflectometer/ellipsometer system is configured such that a polychromatic beam of electromagnetic radiation provided by said source of polychromatic electromagnetic radiation can, optionally, be directed to interact with a sample system present on said stage for supporting a sample system without any polarization state being imposed thereupon, and such that a polychromatic beam of electromagnetic radiation also provided by said source of polychromatic electromagnetic radiation can be, optionally simultaneously, directed to interact with a sample system present on said stage for supporting a sample system after a polarization state has been imposed thereupon. The polychromatic beam of electromagnetic radiation without any polarization state imposed thereupon, when directed to interact with a sample system present on said stage for supporting a sample system, is typically caused to approach said sample system at an oblique angle-of-incidence which is between a sample system Brewster angle and a normal to the surface of the sample system. Further, the polychromatic beam of electromagnetic radiation provided by said source of polychromatic electromagnetic radiation upon which a polarization state has been imposed, is typically directed to interact with a sample system present on said stage for supporting a sample system at an angle near the Brewster angle of the sample system being investigated. Either, or both, the polychromatic beam(s) of electromagnetic radiation provided by said source of polychromatic electromagnetic radiation, upon which is imposed a polarization state or upon which no polarization state is imposed, is preferably directed to interact with a sample system present on said stage for supporting a sample system via a fiber optic means.

As one non-limiting example, the spectroscopic ellipsometer system at least one means for discretely, sequentially, modifying a polarization state of a beam of electromagnetic radiation provided by said source of polychromatic electromagnetic radiation through a plurality of polarization states, can comprise an essentially circular "wheel" element with a plurality of discrete polarization state modifier elements mounted thereupon, on the perimeter thereof, and projecting perpendicularly to a surface of said essentially circular "wheel". The essentially circular "wheel" element further comprises a means for causing rotation about a normal to said surface thereof, such that in use said essentially circular "wheel" element is caused to rotate to position a discrete polarization state modifier element such that the beam of electromagnetic radiation, provided by said source of polychromatic electromagnetic radiation, passes therethrough. That is, the wheel is moved during data collection.

As another non-limiting example, the spectroscopic ellipsometer system at least one means for discretely, sequentially, modifying a polarization state of a beam of electromagnetic radiation provided by said source of polychromatic electromagnetic radiation through a plurality of polarization states, can comprise a plurality of discrete polarization state modifier elements mounted on a slider element which is mounted in a guide providing element. During use sliding the slider element to the right or left serves to position a discrete polarizer element such that said a beam of electromagnetic radiation, provided by said source of polychromatic electromagnetic radiation, passes therethrough.

It is further disclosed that a system for providing an output beam of polychromatic electromagnetic radiation which has a relatively broad and flattened Intensity vs. Wavelength characteristic over a wavelength spectrum utilized in said disclosed invention systems can be applied in the disclosed invention systems. The reason for doing so is to provide an output beam of polychromatic electromagnetic radiation which is substantially a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation. (Note, where colored (LED's) are the sources, said system can utilize their substantially monochromatic outputs as input thereto, perhaps in combination with a white wavelength range (LED)). The system for providing an output beam of polychromatic electromagnetic radiation, which has a relatively broad and flattened intensity vs. wavelength characteristic over a wavelength spectrum, comprises:
- a. at least a first and a second source of polychromatic electromagnetic radiation; and
- b. at least a first electromagnetic beam combining means comprising a plate, (eg. uncoated fused silica or glass etc. such that transmission characteristics thereof are determined by angle-of-incidence and polarization state of a beam of electromagnetic radiation).

The at least a first electromagnetic beam combining means is positioned with respect to said first and second sources of electromagnetic radiation such that a beam of electromagnetic radiation from said first source of electromagnetic radiation passes through said at least a first electromagnetic beam combining means, and such that a beam of electromagnetic radiation from said second source of electromagnetic radiation reflects from said at least a first electromagnetic beam combining means and is comingled with said beam of electromagnetic radiation from said first source of electromagnetic radiation which passes through said at least a first electromagnetic beam combining means. The resultant beam of polychromatic electromagnetic radiation exiting the first electromagnetic beam combining means is substantially an output beam of polychromatic electromagnetic radiation which has a relatively broad and flattened intensity vs. wavelength over a wavelength spectrum, comprising said comingled composite of a plurality of input beams of electromagnetic radiation which individually do not provide such a relatively broad and flattened intensity vs. wavelength over a wavelength spectrum characteristic. Said system for providing an output beam of polychromatic electromagnetic radiation which has a relatively broad and flattened intensity vs. wavelength characteristic over a wavelength spectrum can also be optionally further characterized by a third source of electromagnetic radiation, and a second electromagnetic beam combining (BCM) means comprising an uncoated plate, (eg. fused silica or glass etc. such that transmission characteristics thereof are determined by angle-of-incidence and polarization state of a beam of electromagnetic radiation). The second electromagnetic beam combining means, when present, is positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to the third source of electromagnetic radiation, (when present), such that a beam of electromagnetic radiation from said third source of electromagnetic radiation reflects from said second electromagnetic beam combining means, such that a second resultant beam of polychromatic electromagnetic radiation which is substantially an output beam of polychromatic electromagnetic radiation which has a relatively even more broadened and flattened intensity vs. wavelength over a wavelength spectrum, comprising said comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic.

At least one of said first and second, (when present), electromagnetic beam combining means can be pivotally mounted such that, for instance, the angle at which a beam of electromagnetic radiation from the second source of electromagnetic radiation reflects from the at least one electromagnetic beam combining means can be controlled to place it coincident with the locus of a beam of electromagnetic radiation transmitted therethrough. Pivot means providing two dimensional degrees of rotation freedom are preferred in this application. Further, where sources of electromagnetic radiation can be moved, the pivot capability can be utilized to allow use of optimum tilts of electromagnetic beam combining means. That is, transmission and reflection characteristics of an electromagnetic beam combining means vary with the angle of incidence a transmitted or reflected beam makes with respect thereto, and pivot means can allow adjusting tilt to optimize said characteristics.

Further, as the polarizer in the present invention spectroscopic ellipsometer system remains essentially fixed in position during data acquisition, it is noted that it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between "S" polarization transmission and reflection components is less, as a function of wavelength and electromagnetic beam angle-of-incidence to said beam combining means, when compared to that of the "P" components. The "P" component is far more affected, particularly around a Brewster angle condition, hence, where an "S" component, with reference to a beam combining system, is utilized, it is to be appreciated that variation in intensity of transmitted and reflected beams of electromagnetic radiation output from the beam combining system, as functions of wavelength and the angles of incidence of beams of electromagnetic radiation from sources of said transmitted and reflected beams of electromagnetic radiation, is minimized, as compared to variation which occurs in "P" components.

Before discussing the Method of Calibration of the present invention spectroscopic ellipsometer system, it is noted that the polarizer and analyzer thereof, which are essentially fixed in position during data acquisition, are not necessarily absolutely fixed in position. Said polarizer and analyzer are preferably what is properly termed "Rotatable". That is they can be rotated to various positions by a user between data acquisitions, but they are not caused to be Rotating while data is being acquired. (Typical positioning of analyzer and polarizer azimuthal angles are plus or minus forty-five (+/−45) degrees).

Continuing, a present invention method of calibrating a spectroscopic ellipsometer system comprising the steps of:

a. providing a spectroscopic ellipsometer system as described above herein, either independently or in functional combination with a reflectometer system;

said method further comprising, in any functional order, the steps of:

b. for each of at least two ellipsometrically different sample systems, obtaining at least one multi-dimensional data set(s) comprising intensity as a function of wavelength and a function of a plurality of discrete polarization state settings, (which can be set by sequentially energizing different sources, or by placing polarization state modifiers into the path of a beam from a single source);

c. providing a mathematical model of the ellipsometer system and sample systems utilized, including accounting for the polarization state settings utilized in step b; and d. by simultaneous mathematical regression onto said data sets, evaluating parameters in said mathematical model.

It is noted that the step of providing a means for discretely, sequentially, modifying a polarization state of a beam of electromagnetic radiation provided by said source of polychromatic electromagnetic radiation through a plurality of polarization states, can involve:

providing at least one such means for discretely, sequentially, modifying a polarization state of a beam of electromagnetic radiation provided by a source of polychromatic electromagnetic radiation through a plurality of polarization states that changes the phase angle between orthogonal components of said electromagnetic beam of radiation; or providing at least one such means for discretely, sequentially, modifying a polarization state of a beam of electromagnetic radiation provided by a source of polychromatic electromagnetic radiation through a plurality of polarization states, that changes the magnitude intensity of least one orthogonal component of said electromagnetic beam of radiation; or providing at least one such means for discretely, sequentially, modifying a polarization state of a beam of electromagnetic radiation provided by a source of polychromatic electromagnetic radiation through a plurality of polarization states, that changes both the phase angle between orthogonal components and the magnitude of least one orthogonal component of said electromagnetic beam of radiation; or energizing separate sources of electromagnetic radiation, each of which has a different polarization state associated therewith, all of which provide an electromagnetic beam which approaches a sample system along a common locus via beam combiners.

It is also mentioned that said method of calibrating a spectroscopic ellipsometer system can require, in the step b. obtaining of at least one multi-dimensional data set(s) comprising intensity as a function of wavelength and a function of a plurality of discrete polarization settings, the obtaining of data from at least as many sample systems as are utilized discrete polarization state settings. However, if polarization state characteristics are parameterized, say as a function of wavelength, and are expressed by equations with a minimized number of parameters therein, it is possible to reduce the number of sample systems which must be utilized.

In step b. of said procedure the various polarization states can be set utilizing the previously described essentially circular "wheel" element with a plurality of discrete polarizer elements mounted thereupon on the perimeter thereof, or can comprise the previously described slider element with plurality of discrete polarizer elements mounted thereupon, or using any functionally equivalent means to place the polarization state modifier into the pathway of a beam of electromagentic radiation.

It is noted that polarization state modifiers variously cut from, for instance, low-cost plastic sheets, can be sequentially positioned into the path of a beam of electromagnetic radiation, via a stepper motor. It is noted that it is primarily the presence of a plurality of separate sources, or at least one means for transmissively, discretely, sequentially varying polarization states in a beam of polychromatic electromagnetic radiation in the ellipsometer portion of a present invention system, which distinguishes the present invention system over previous spectroscopic ellipsometer systems which contain continuously rotating means for changing polarization states in a beam of polychromatic electromagnetic radiation.

Practice can also involve positioning input and output polarizer/analyzer system azimuthal angles at typical fixed, nominal, constant plus or minus forty-five (+/−45) degrees, although use of polarizer and analyzer elements which are rotatable between data acquisition procedures is acceptable. It is noted that the static positioning of said input and output polarizer/analyzer system azimuthal angles greatly simplifies data acquisition, in that no phase sensors are required to detect rotational positioning are necessary, because synchronization is unnecessary. That is, as ellipsometric data is acquired asynchronously, the system requirements are greatly reduced as compared to ellipsometer systems which involve elements that are caused to rotate during data acquisition. Also, as alluded to, fiber optics can be utilized for transporting electromagnetic radiation to and from the ellipsometer system portion of the present invention. The foregoing points make it possible to retro-fit mount the ellipsometer portion of the present invention to existing spectroscopic reflectometer systems, (such as those presently marketed by Nanometrics Inc.), in a manner that optionally involves sharing of a source of electromagnetic radiation and/or detector system thereof with said ellipsometer system.

While the foregoing has disclosed present invention systems, it remains to describe the mathematical basis for practicing the present invention. As described, the present Descrete Polarization State Spectroscopic Ellipsometer (DSP-SE$_{tm}$) system comprises:

multiple sources which each include transmissive polarization state setting means to provide different polarization states when sequentially energized, a stage for supporting a sample system with a sample system present thereupon, an analyzer, and a means for detecting beam intensity, (eg. a detector system); or a source of polychromatic electromagnetic radiation, an optical element for setting a polarization state, (eg. a polarizer), a stage for supporting a sample system with a sample system present thereupon, a means for discretely, sequentially, modifying a polarization state of a beam of electromagnetic radiation provided by said source of polychromatic electromagnetic radiation through a plurality of polarization states by passage therethrough, an analyzer, and a means for detecting beam intensity, (eg. a detector system).

As indicated, in practice an input element is typically a polarizer with its transmission axis oriented approximately +45 or −45 degrees from the sample system plane of incidence. Using Mueller Matrix/Stokes Vector Calculus, the input beam passing through such a polarizer is represented by:

$$I_P = \begin{pmatrix} 1 \\ \cos(2P) \\ \sin(2P) \\ 0 \end{pmatrix}$$

where "P" is the azimuthal angle of the polarizer with respect to the sample plane of incidence. For optimal performance over a wide range of sample systems, and computational simplicity, the "p" is usually chosen to be +/−45 degrees, and the Stokes Vector becomes:

$$I_P = \begin{pmatrix} 1 \\ 0 \\ \pm 1 \\ 0 \end{pmatrix}$$

Now, an isotropic sample can be optically modeled by the Mueller Matrix:

$$M_S = \begin{pmatrix} 1 & -N & 0 & 0 \\ -N & 1 & 0 & 0 \\ 0 & 0 & C & S \\ 0 & 0 & -S & C \end{pmatrix}$$

and the Stokes Vector resulting from a polarized polychromatic electromagnetic radiation beam interaction with a sample system is described by:

$$M_S \cdot I_P = \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ 0 \\ \pm 1 \\ 0 \end{pmatrix} = \begin{pmatrix} 1 \\ -N \\ C \cdot \pm 1 \\ -S \cdot \pm 1 \end{pmatrix}$$

A generalized polarization state modifier (PSM) element, (which can comrpise a combination of elements), followed by a polarization state insensitive detector yields the following Stokes Vector:

$$PSM = (1\ 0\ 0\ 0) \cdot \begin{pmatrix} m00 & m01 & m02 & m03 \\ m10 & m11 & m12 & m13 \\ m20 & m21 & m22 & m23 \\ m30 & m31 & m32 & m33 \end{pmatrix} = (m00\ m01\ m02\ m03)$$

therefore, if there are "n" discrete polarization states, the beam intensity measured for the "n'th" polarization state is:

$$I_n = PSM_n \cdot M_S \cdot I_P$$

$$= (m0_n\ m1_n\ m2_n\ m3_m) \cdot \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ 0 \\ \pm 1 \\ 0 \end{pmatrix}$$

$$= m0_n - m1_n \cdot N + (m2_n \cdot C - m3_m \cdot S) \cdot \pm 1$$

The transfer matrix for traditional 4-detector polarimeter systems is constructed by inserting the (PSM) into "rows" which correspond to the polarization state measured by each detector:

$$I_n = A \cdot S$$

$$\begin{pmatrix} I_0 \\ I_1 \\ I_2 \\ I_3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix} \cdot \begin{pmatrix} 1 \\ -N \\ C \cdot \pm 1 \\ -S \cdot \pm 1 \end{pmatrix}$$

If the "A" transfer matrix is invertable, (ie. the determinate is non-zero), it can be concluded that sample system's N, C and S ellipsometric parameters can be determined from the measured intensities at each detector.

$$\begin{pmatrix} 1 \\ -N \\ C \cdot \pm 1 \\ -S \cdot \pm 1 \end{pmatrix} = A^{-1} \cdot \begin{pmatrix} I_0 \\ I_1 \\ I_2 \\ I_3 \end{pmatrix}$$

Furthermore, in a traditional 4-detector polarimeter system, the "A" transfer matrix is determined, (at each wavelength of operation), by inputting a series of known polarization states and measuring the resulting intensities at each detector.

While the present invention (DSP-SE$_{tm}$) is similar to traditional 4-detector polarimeter systems, it differs in that more than 4 polarization states can optionally be incorporated into the measurement. The "A" matric therefore is generally not "square", and a simple inversion can not be used to directly extract sample system N, C and S ellipsometic parameters. Regression analysis based on known optical models can also be used to determine, (ie. calibrate), the "A" transfer matrix of the system, and to extract the ellipsometric parameters from the "n" measuremed intensities.

While many variations are possible, in the preferred, non-limiting, embodiment of the present invention the (DSP-SE$_{tm}$) the input polarizer, as mentioned, is fixed at 45 degrees, such that the Stokes Vector which enters the polarimeter after interaction with the sample system is given by:

$$M_S \cdot I_P = k \cdot \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ 0 \\ 1 \\ 0 \end{pmatrix} = k \cdot \begin{pmatrix} 1 \\ -N \\ C \\ -S \end{pmatrix}$$

(where "k" is an arbitrary constant which accounts for the unknown intensity provided by the source of polychromatic electromagnetic radiation).

For the 1st discrete polarization state of the detector system, a polarizer, (typically termed an analyzer when placed after the sample system), with the azimuthal angle threof set at 45 degrees, the detected intensity is of the form:

$$I_0 = PSM_0 \cdot M_S \cdot I_P = (1\ 0\ -1\ 0) \cdot k \cdot \begin{pmatrix} 1 \\ -N \\ C \\ -S \end{pmatrix} = k \cdot (1 - C)$$

For the next two discrete polarization states, a quarter-wave retarder can be inserted in front of the analyzer, at azimuthal angles of zero (0.0) and ninety (90) degrees respectively, to provide:

$$I_1 = PSM_1 \cdot M_S \cdot I_P$$

$$= (1\ 0\ -1\ 0) \cdot \begin{pmatrix} 1 & 0 & 0 & 0 \\ 0 & 1 & 0 & 0 \\ 0 & 0 & 0 & 1 \\ 0 & 0 & -1 & 0 \end{pmatrix} \cdot k \cdot \begin{pmatrix} 1 \\ -N \\ C \\ -S \end{pmatrix}$$

$$= k \cdot (1 + S)$$

(for retarder @ 0°)

$$I_2 = PSM_2 \cdot M_S \cdot I_P$$

$$= (1\ 0\ -1\ 0) \cdot \begin{pmatrix} 1 & 0 & 0 & 0 \\ 0 & 1 & 0 & 0 \\ 0 & 0 & 0 & -1 \\ 0 & 0 & 1 & 0 \end{pmatrix} \cdot k \cdot \begin{pmatrix} 1 \\ -N \\ C \\ -S \end{pmatrix}$$

$$= k \cdot (1 - S)$$

(for retarder @ 90°)

For two additional discrete polarization states, a quarter-wave retarder can be inserted in front of the analyzer, at azimuthal angles of +/−twenty-two (22) degrees, respectively, to provide:

$$I_3 = PSM_3 \cdot M_S \cdot I_P$$

$$= (1 \ 0 \ -1 \ 0) \cdot \begin{pmatrix} 1 & 0 & 0 & 0 \\ 0 & \frac{1}{2} & \frac{1}{2} & \frac{-1}{2} \cdot \sqrt{2} \\ 0 & \frac{1}{2} & \frac{1}{2} & \frac{1}{2} \cdot \sqrt{2} \\ 0 & \frac{1}{2} \cdot \sqrt{2} & \frac{-1}{2} \cdot \sqrt{2} & 0 \end{pmatrix} \cdot k \cdot \begin{pmatrix} 1 \\ -N \\ C \\ -S \end{pmatrix}$$

$$= \left(1 - \frac{1}{2} \cdot C + \frac{1}{2} \cdot N + \frac{1}{2} \cdot \sqrt{2} \cdot S\right) \cdot k$$

(for retarder @ +22.5°)

$$I_4 = PSM_4 \cdot M_S \cdot I_P$$

$$= (1 \ 0 \ -1 \ 0) \cdot \begin{pmatrix} 1 & 0 & 0 & 0 \\ 0 & \frac{1}{2} & \frac{-1}{2} & \frac{1}{2} \cdot \sqrt{2} \\ 0 & \frac{-1}{2} & \frac{1}{2} & \frac{1}{2} \cdot \sqrt{2} \\ 0 & \frac{-1}{2} \cdot \sqrt{2} & \frac{-1}{2} \cdot \sqrt{2} & 0 \end{pmatrix} \cdot k \cdot \begin{pmatrix} 1 \\ -N \\ C \\ -S \end{pmatrix}$$

$$= \left(1 + \frac{1}{2} \cdot \sqrt{2} \cdot S - \frac{1}{2} \cdot N - \frac{1}{2} \cdot C\right) \cdot k$$

(for retarder @ −22.5°)

Simple combinations of these intensities yield:

$$I_0 = k \cdot (1 - C)$$
$$I_1 - I_2 = 2 \cdot k \cdot S$$
$$I_1 + I_2 = 2 \cdot k$$
$$I_3 - I_4 = k \cdot N$$

from which sample system N, C, S, and are easily derived as:

$$N = 2 \cdot \frac{I_3 - I_4}{I_1 + I_2}$$
$$C = \frac{(I_1 + I_2 - 2 \cdot I_0)}{(I_1 + I_2)}$$
$$S = \frac{(I_1 - I_2)}{(I_1 + I_2)}$$
$$\Delta = \operatorname{atan}\left(\frac{S}{C}\right)$$
$$\Psi = \frac{1}{2} \cdot \operatorname{atan}\left(\frac{\sqrt{C^2 + S^2}}{N}\right)$$

While the math for the preceeding 5-state (DSP-SE$_{tm}$) system is elegant, a potential difficulty in implementing said design is that insertion of the quarter-wave plates to effect polarization states 1–4, introduces intensity loss as a result of reflection from the optical element surface, which is not present when obtaining the first data set wherein no quarter-wave plate is present. This additional intensity loss must be accounted for in the calibration algorithm. A modified approach involves not obtaining or not utilizing the first data set. While this slightly complicates the equations, a simple analytic solution is still possible and values for N, C and S can be derrived as:

$$I_1 - I_2 = 2 \cdot k \cdot S$$
$$I_1 + I_2 = 2 \cdot k$$
$$I_3 - I_4 = k \cdot N$$
$$I_3 + I_4 = \left(2 - C + \sqrt{2} \cdot S\right) \cdot k$$
$$N = 2 \cdot \frac{(I_3 - I_4)}{(I_1 + I_2)}$$
$$C = \frac{(2 - \sqrt{2}) \cdot I_2 + (2 + \sqrt{2}) \cdot I_1 - 2 \cdot (I_3 + I_4)}{(I_1 + I_2)}$$
$$S = \frac{(I_1 - I_2)}{(I_1 + I_2)}$$

A more general 4-state (DSP-SE$_{tm}$) approach utilizes an input polarizer, an output analyzer and four (4) retarder elements at various azimuthal orientations. In this approach, while the azimuthal orientations for the optical elements are nominally chosen to be the same as in the preceeding design, arbitrary azimuthal orientations as well as non-ninety degree retardation values are allowed. Under this approach, the Stokes Vector provided to the Polarimeter is given by:

$$I_{S,P} = \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ \cos(2P) \\ \sin(2P) \\ 0 \end{pmatrix}$$

$$= \begin{pmatrix} 1 - N \cdot \cos(2 \cdot P) \\ -N + \cos(2 \cdot P) \\ C \cdot \sin(2 \cdot P) \\ -S \cdot \sin(2 \cdot P) \end{pmatrix}$$

$$= \begin{pmatrix} s0 \\ s1 \\ s2 \\ s3 \end{pmatrix}$$

(where "P" is the input polarimeter azimuth).

The response of each discrete polarization state "n" to an input Stokes Vector is:

$$1_n = (m0_n \quad m1_n \quad m2_n \quad m3_n)$$  (DPS #2)

$$m0_n = 1$$
$$m1_n = (cr_n \cdot sr_n - c\delta_n \cdot sr_n \cdot cr_n) \cdot S2A + (cr_n)^2 +$$
$$\qquad c\delta_n \cdot (sr_n)^2 \cdot C2A$$
$$m2_n = [(sr_n)^2 + c\delta_n \cdot (cr_n)^2] \cdot S2A +$$
$$\qquad (sr_n \cdot cr_n - c\delta_n \cdot cr_n \cdot sr_n) \cdot C2A$$
$$m3_n = (S2A \cdot cr - C2A \cdot sr) \cdot s\delta$$

where $cr=\cos(2r)$, $sr=\sin(2r)$, $s\delta\sin(\delta)$, $C2A=\cos(2A)$, $S2A=\sin(2A)$, r is the retarder azimuthal orientation angle, $\delta$ is the retardance, and A is the analyzer orientation.

(for most retarders, the retardance varies inversely with wavelength, that is $\delta(\lambda)=\delta_c/\lambda$)

These polarization state modifying vectors can be packed into a (4×4) square transfer matrix "A", such that the measured intensity for each discrete state is given by:

$$I_n = A \cdot I_{S,P} = \begin{pmatrix} I_0 \\ I_1 \\ I_2 \\ I_3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix} \cdot \begin{pmatrix} s0 \\ s1 \\ s2 \\ s3 \end{pmatrix}$$

To determine the Stokes Vector incident on the Polarimeter, the transfer matrix "A" s inverted and multiplied times the measured intensities coresponding to each discrete polarization state:

$$\begin{pmatrix} s0 \\ s1 \\ s2 \\ s3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix}^{-1} \cdot \begin{pmatrix} I_0 \\ I_1 \\ I_2 \\ I_3 \end{pmatrix}$$

and the sample system parameters:

$$N = \cos(2 \cdot P) - s1$$

$$C = \frac{s2}{\sin(2 \cdot P)}$$

$$S = \frac{-s3}{\sin(2 \cdot P)}$$

can then be extracted. To illustrate this approach, a transfer matrix is constructed assuming nominal azimuthal orientations of (0.0), (90) (+22.5) and (−22.5) degrees for each of the four (4) discrete polarization states. The same nominal retardance is assumed for each retarder. The analytical inversion of this matrix is very complicated, but it is still trivial to numerically invert the matrix given the sample expressions for each element given by:

Multiplying the inverted matrix by the measured intensities for each discrete polarization state allows straight forward determination of the sample system characterizing N, C, S, $\Psi$, and $\Delta$.

A General Regression Based Approach to Calibration of (DSP-SE$_{tm}$) systems and allow extraction of accurate ellipsometric sample system characterizing data assumes that the (DSP-SE$_{tm}$) system measures polychromatic electromagnetic radiation beam intensity at "n" discrete polarization states, and that "m" samples with different ellipsometric properties are utilized. For a traditional polarimeter system, which is calibrated on a wavelength by wavelength basis, it is necessary to have "m" be greater than or equal to "n". However, utilizing global regression which allows calibration parameters to be parameterized vs. wavelength, (thereby reducing the number of parameters required to describe the system transfer Matrices "A" at each wavelength), it is possible to reduce the number of calibration sample systems required, "m", to be less than "n". Under this approach, calibration of a present invention (DSP-SE$_{tm}$) system, a multi-dimensional data set "I" is measured consisting of measured polychromatic electromagnetic radiation beam intensities for each discrete polarization state, on each calibration sample system, and at each wavelength in the spectral range of the instrument:

$$Igen(p_y)_{i,j,k} = A \cdot \begin{pmatrix} 1 & -N_{j,k} & 0 & 0 \\ -N_{j,k} & 1 & 0 & 0 \\ 0 & 0 & C_{j,k} & S_{j,k} \\ 0 & 0 & -S_{j,k} & C_{j,k} \end{pmatrix} \cdot \begin{pmatrix} s_0 \\ s_1 \\ s_2 \\ s_3 \end{pmatrix}$$

To generate "predicted" intensities measured by the (DSP-SE$_{tm}$), (as a function of calibration parameters spsecified in the vector $p_y$), the following equation is applied:

$[\exp_{i,j,k}$ where $i = 1 \ldots n$ (for each discrete polarization state)

$j = 1 \ldots m$ (for each calibration sample)

$k = 1 \ldots w$ (for each wavelength)

where "A" is an ("n"×4) matrix, in which each row is possibly parameterized by foregoing equation DSP#2 and the input vector s is possibly parameterized by the input polarizer azimuth by an equation DSP#1. The extraction of calibration sample system's N, C and S parametres can be calculated as a function of film thickness and angle of incidence (given calibration sample systems which are well characterized by known optical models and optical constants, such as SiO$_2$ on Si films with systematically increasing SiO$_2$ film thicknesses).

$$A = \begin{bmatrix} 1 & C2A & c\delta \cdot S2A & S2A \cdot s\delta \\ 1 & C2A & c\delta \cdot S2A & -(S2A \cdot s\delta) \\ 1 & (1-c\delta) \cdot \frac{S2A}{2} + (1+c\delta) \cdot \frac{C2A}{2} & (1+c\delta) \cdot \frac{S2A}{2} + (1-c\delta) \cdot \frac{C2A}{2} & (S2A - C2A) \cdot s\delta \cdot \frac{\sqrt{2}}{2} \\ 1 & -(1-c\delta) \cdot \frac{S2A}{2} + (1+c\delta) \cdot \frac{C2A}{2} & (1+c\delta) \cdot \frac{S2A}{2} - (1-c\delta) \cdot \frac{C2A}{2} & (S2A + C2A) \cdot s\delta \cdot \frac{\sqrt{2}}{2} \end{bmatrix}$$

To perform regression analysis, the "chi-squared" function:

$$\chi^2 = \sum_{i=1}^{n} \sum_{j=1}^{m} \sum_{k=1}^{w} \left[ \frac{I\exp_{i,j,k}}{\sqrt{\sum_{i=1}^{m}(I\exp_{i,j,k})^2}} - \frac{Igen(p_y)_{i,j,k}}{\sqrt{\sum_{i=1}^{m}(Igen(p_y)_{i,j,k})^2}} \right]^2$$

is then minimized, (typically utilizing a non-linear regression algorithm such as "Marquard-Levenberg"), by adjusting calibration parameters specified in the vector "$p_y$". To aid in the regression, both the experimental and generated intensity vectors are normalized by the sum of the squares of all the discrete polarization states at each wavelength.

If the global parameterization of calibration parameters is not used, then the vector "$p_y$" consists of the input Stokes Vector values "$s_n$", and the elements of the transfer matrix "A", all of which must be defined at each wavelength, This requires at least $(4+(4\times n))\times w)$ calibration parameters, assuming that the ellipsometric parameters (N, C and S), for each calibration sample system are exactly known.

Further, if global parameterization is used, the input vector "$s_n$" for all wavelengths can be parameterized by the input polarizer azimuth "P", the ellipsometric parameters of the "m" calibration samples can be parametrically calculated as a function of angle of incidence ($\Theta$) and film thickness "$t_m$", and the transfer matrix "A" can be parameterized by the Azimuth of the analyzer "A", the orientation of each retarder "$r_n$", and the retardance of each retarder as a function of wavelength $\delta(\lambda)_n = \delta c_n/\lambda$. It is noted that higher order terms could also be added to the retardance vs. wavelength function, or to any other of the calibration parameters to improve fit between the experimentally measured and modeled generated data. Such a global parameterization significantly reduces the number of calibration parameters required to describe the (DSP-SE$_{tm}$) system over a spectroscopic range of wavelengths. The total number of calibration parameters in this suggested parameterization (other variations are certainly possible as well), may be as few as:

$p_y = P + \phi_m + t_m + A + r_n + \delta c_\infty = 1 + m + m + 1 + n + m = (2 \times m) + (2 \times n) + 2$.

To extract the ellipsometric parameters of an arbitrary sample system which is inserted into a general (DSP-SE$_{tm}$) system, a regression analysis can also be performed, and N, C and S can be defined and evaluated by regression at each wavelength separately.

Further, if the plane of incidence of the sample system is allowed to vary slightly, (to account for imperfect alignment to the ellipsometer system), the Stokes Vector which enters the discrete polarization state modifier becomes:

$$M_S \cdot I_P = k \cdot \begin{pmatrix} 1 & 0 & 0 & 0 \\ 0 & \cos(s) & -\sin(s) & 0 \\ 0 & \sin(s) & \cos(s) & 0 \\ 0 & 0 & 0 & 1 \end{pmatrix} \cdot \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 & 0 & 0 & 0 \\ 0 & \cos(s) & \sin(s) & 0 \\ 0 & -\sin(s) & \cos(s) & 0 \\ 0 & 0 & 0 & 1 \end{pmatrix} \cdot \begin{pmatrix} 1 \\ 0 \\ 1 \\ 0 \end{pmatrix}$$

$$= k \cdot \begin{bmatrix} 1 - s \cdot N \\ -N + s \cdot (1 - C) \\ -s \cdot N + C \\ -S \end{bmatrix}$$

where "s" is the azimuthal misalignment of the sample system, and presumably is very near zero.

In this case the (DSP-SE$_{tm}$) system, would not measure the "true" N, C and S parameters, but would instead measure "effective" parameters Neff, Ceff and Seff:

$$Neff = N - s \cdot (1 - C)$$
$$Ceff = C - s \cdot N$$
$$Seff = S$$

It would be possible to include the azimuthal misalignment factor "s" as a fitting parameter in subsequent analysis of the ellipsometric data measured by a (DSP-SE$_{tm}$) system.

It is believed that the present invention spectroscopic ellipsometer system combination comprising:
  no moving elements during data acquisition; and
  means for discretely, sequentially, providing
    a beam of electromagnetic radiation which is sequenced through plurality of polarization states, said means being a plurality of sources which are sequentially energized, or means present at at least one location selected from the group consisting of:
      between said polarizer and said stage for supporting a sample system; and
      between said stage for supporting a sample system and said analyzer;

said at least one means discretely, sequentially providing a beam of electromagnetic radiation which demonstrates a plurality of non-continuously changing polarization states;

is Patentably distinct over all prior art.

Patentability is thought to be further enhanced when (LED's) are utilized, and where the source of polychromatic radiation comprises a system for providing an output beam of polychromatic electromagnetic radiation, which has a relatively broad and flattened intensity vs. wavelength characteristic over a wavelength spectrum. Said result can be achieved by application of a system which comprises at least a first and a second source of polychromatic electromagnetic radiation; and at least a first electromagnetic beam combining means comprising a plate, (eg. uncoated fused silica or glass etc. such that reflection/transmission characteristics thereof are determined by angle-of-incidence and polarization state of a beam of electromagnetic radiation). A similar relatively broad and flattened intensity vs. wavelength characteristic result can be achieved by application of a Beam Chromatic Shifting and Directing Means (ZCM) which comprises a Silicon Substrate (SI) upon the surface of which is present between about 500 and 1500 Angstroms, (nominal 600 or 1200 Angstroms), of Silicon Dioxide (SIO2).

It is also noted that while better presented in Co-Pending application Ser. No. 09/945,962 from which this Application is a CIP, Sequential Discrete Polarization States can be set by at least one Rotatable Compensator, preferably as mounted in a hollow shaft suitable for control by a stepper motor. Such a configuration is known for Polarizers and Analyzers, but is not known for Compensators.

Also, it is noted that detection can be emphasized in Electromagnetic Spectrum IR and UV wavelengths by reflecting a beam substantially centered in the Visual, off such as a Silicon Substrate with, for example 500–1500 Angstroms of SiO2 present on the surface thereof. Suitable Detectors can include a Grating/Prism and a Diode Array, or a single detector for spectroscopic and monchromatic wavelengths, respectively.

It is also noted that selection of discrete polarization states can be made on the basis of the characteristics of a Sample, such that Sample properties can be better evaluated.

The present invention will be better understood by reference to the Detailed Description Section of this Specification, in combination with the Drawings.

SUMMARY

It is therefore a primary purpose and/or objective of the present invention to disclose a low cost spectroscopic ellipsometer system which comprises a plurality of discrete, separately energizable sources of electromagnetic radiation, each of which has associated therewith a separate means for setting a polarization state onto the beam of electromagnetic radiation provided by one of said sources.

It is yet another purpose and/or objective of the present invention to disclose use of a beam splitting analyzer in said low cost spectroscopic ellipsometer system which, in use, has no moving parts.

It is another purpose and/or objective yet of the present invention to disclose preferred, but not limiting, sources of electromagnetic radiation as being light emitting diodes, in particular wide band white light emitting diodes.

It is another purpose and/or objective of the present invention to disclose methodology of application of said low cost spectroscopic ellipsometer system in which the source of a plurality of polarizatin states has no moving parts during data collection.

It is another purpose and/or objective of the present invention to disclose use of a beam combining means for combining multiple beams of electromagnetic radiation to form a more unifirm intensity vs. wavelength source, in a low cost spectroscopic ellipsometer system.

Other purposes and/or objectives will become clear from a reading of the Specification and Claims.

BRIEF DESCRIPTION OF THE DRAWINGS

FIG. 3a shows a frontal perspective view of a discrete state polarizer comprising a wheel with five discrete polarizer elements mounted thereupon.

FIG. 3b shows a side elevational view of a discrete state polarizer, as in FIG. 3a, oriented so that an electromagnetic beam passing through one of the discrete polarizer five elements.

FIG. 3c shows a front elevational view of a discrete state polarizer with five laterally slideably mounted discrete polarizer elements mounted therein.

FIG. 3d1 shows a system for providing an output beam (OB) or (OB') of polychromatic electromagnetic radiation which has a relatively broad and flattened intensity vs. wavelength characteristic over a wavelength spectrum.

FIGS. 3d2 and 3d3 show an alternative system for emphasizing IR and UV wavelength Spectrum Intensity.

FIG. 4a demonstrate flow of use of the present ivnention.

FIG. 4b demonstrates the flow of a present invention method of calibration of the present invention spectroscopic ellipsometer.

DETAILED DESCRIPTION

Figure 1A:
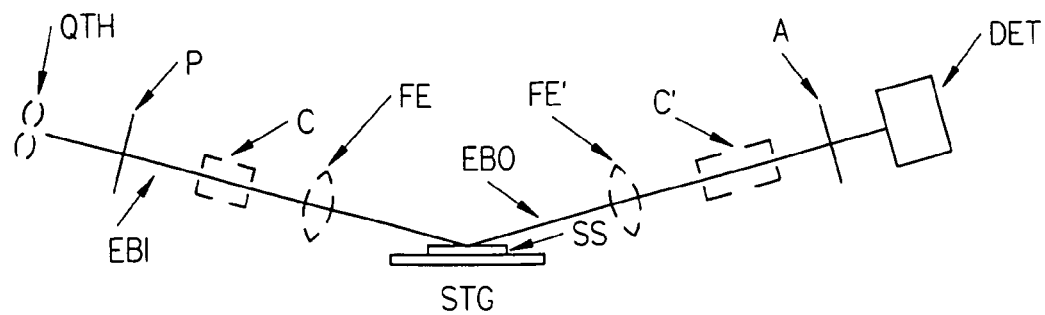
FIG. 1a shows a typical spectroscopic ellipsometer system configuration.

Turning now to FIG. 1a, there is shown a representation of a typical spectroscopic ellipsometer system configuration. Shown are a source of polychromatic electromagnetic radiation (QTH), (eg. a quartz tungsten-halogen-lamp), a polarizer (P), an optional Compensator (C), a stage for supporting a sample system (STG) with a sample system (SS) present thereupon, an optional Compensator (C), an analyzer (A), and a detector system (DET). Note detector systems can be spectroscopic multi-element such as Bucket Brigade, Diode and CCD arrays and that "off-the-shelf" spectrometer systems such as manufactured by Zeiss can also be applied). Shown also are ellipsometer electromagnetic beam in (EBI) and ellipsometer electromagnetic beam out (EBO). Further are shown Focusing and Collimating Lenses (FE) (FE'), which are preferably achromatic. In use at least one of the Polarizer and/or Analyzer and/or Compensator is caused to rotate during data acquisition.

Figure 1B:
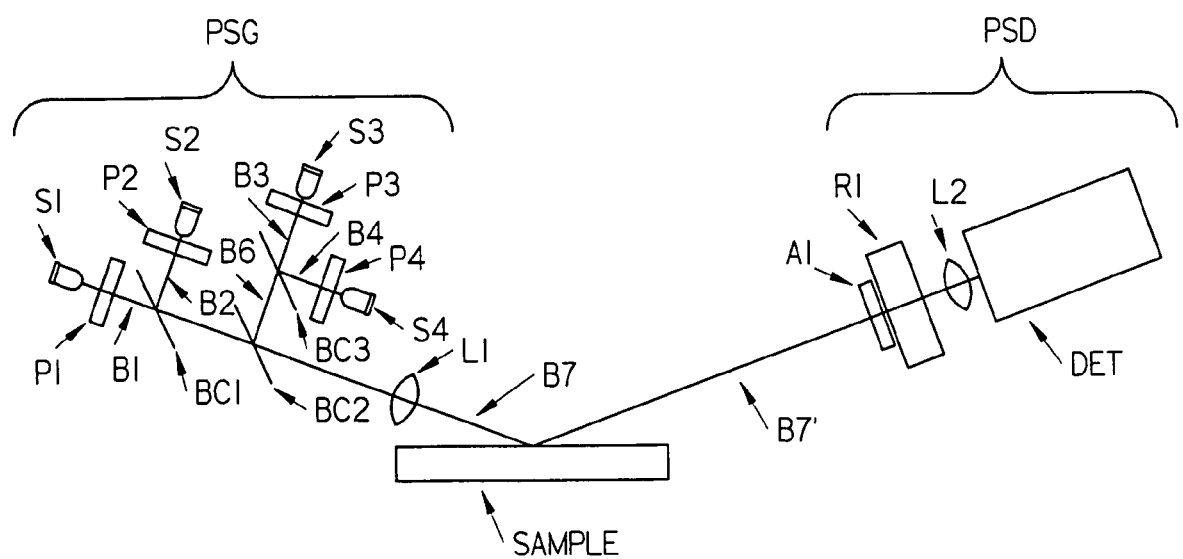
FIG. 1b shows a prefered disclosed invention spectroscopic ellipsometer system configuration.

In contrast to the system shown in FIG. 1a, FIG. 1b shows a prefered presently disclosed low cost spectroscopic ellipsometer system configuration, which in use during data acquisition has no moving parts. Shown are Sources of electromagnetic radiation (S1), (S2), (S3) and (S4), each having an associated Polarizer Means (P1), (P2), (P3) and (P4), respectively, associated therewith. (For instance, the Polarization States imposed by (P1), (P2), (P3) and (P4) can be selected to be −45, 0.0, +45 and 90 Degrees respectively). Also shown are Beam Combining Means (BC1) and (BC2). Note that Beam Combining Means (BC1) serves to combine Beams of electromagnetic Radiation (B1) and (B2) from Sources (S1) and (S2) respectively, and produce Beam (B5). Note that Sources (S1) and (S2) have Polarization Means (P3) and (P4) associated therewith. Continuing, Beam (B5) enters Beam Combiner Means (BC2), which also receives Beam (B6), said Beam (B6) being a combination of beams (B3) and (B4) which exits Beam Combiner (BC3). Beam (B7) exits Beam Combiner (BC2) and passes through Lens (L1) before impinging onto the Sample. The pathways from each sources of electromagnetic radiation (S1), (S2), (S3) and (S4) should be noted are preferably selected to be substantially equal to the point of interacting with the Sample. (Note that elements (S1), (S2), (S3) and (S4); (P1), (P2), (P3) and (P4), (BC1), (BC2) and (BC3) and (L1) in combination are sometimes refered to as a Polarization State Generator (PSG)). Reflected Beam (B7') is shown entering a Detector (DET) via a functionally combined Analyzer (A1) and Rotation Stage (R1). (The rotation statge allows for setting multiple Analyzer (A) azimuthal settings during system calibration). Also shown is a Lens (L2) which focuses electromagnetic radiation onto the Detectro (DET). (For instance, in use where (P1), (P2), (P3) and (P4) can be selected to be −45, 0.0, +45 and 90 Degrees respectively, (R1) might be set to orient the azimuth of (A1) at +45 degrees). (Note that said elements (A1), (R1) (L2) and (DET) are sometimes refered to as a Polarization State Detector (PSD)).

Figure 1C:
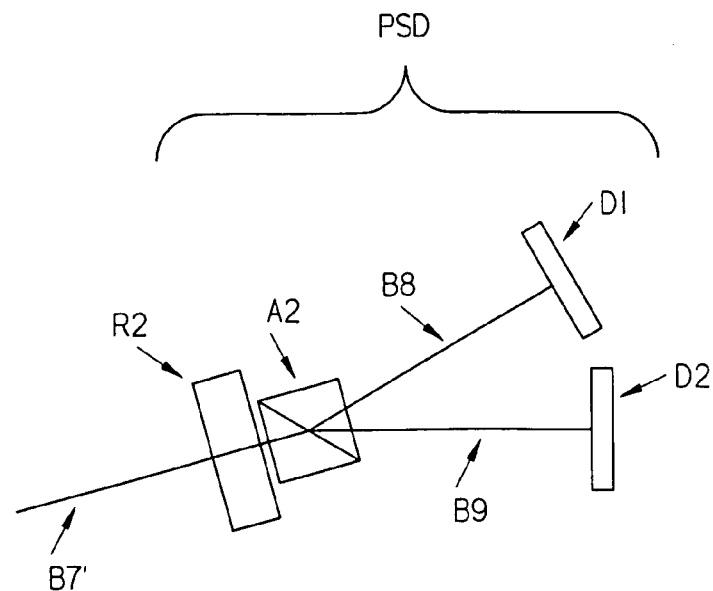
FIG. 1c shows a Detector suitable for use with the FIG. 1b spectroscopic ellipsometer system.

FIG. 1c better shows a Polarization State Detector (PSD) which is suitable for use with the FIG. 1b spectroscopic ellipsometer system. It comprises a functionally combined Rotation Stage (R2) and a Beam Splitting Analyzer (A2), which Beam Splitting Analyzer (A2) outputs two Polarization State Dependent Beams, (B8) AND (B9), which are intercepted by Detectors (D1) and (D2), respectively.

As described in the Disclosure of the Invention Section, in use the various Sources (S1), (S2), (S3) and (S4) are sequentially energized to sequentially provide Beam (B7), which has a progression of polarization states dependent on which Source was energized. It should be apparent that with no moving parts required, a sequence of polarization states can then be sequentially presented to the Sample. This is considered a very important aspect of the prefered embodiment of the disclosed invenion.

In the disclosed invention, multiple light sources are applied to generate different polariation states which are utilized in characterizing a Sample. While conventional ellipsometer Sources, (eg. Lasers and Arc Lamps), are expensive, Light Emitting Diodes, (LED's) are readily avalable and inexpensive, (typically less than $5.00 each). In addition, (LED's) are Solid Statem, have no moving parts, generate very little heat, are highly efficient and have very long lifetimes (eg. greater than 100,000 hours). Further, as alluded to, (LED's) can be modulated, (ie. turned on and off). While discrete wavelength (LED's) have been available for years, it is only relatively recently that white (LED's), which produce wavelengths throughout the Visible Range, have become available. While not productive of as intense an output as conventional Sources, and not allowing for as high a degree of collimation, the compact design of spectroscopic ellipsometers enabled by their use facilitates realization of ellipsometer systems with divergence minimizing short beam pathlengths therefrom to a sample.

It is also noted that use of colored output (LED's) results in even lower costs than does use of White (LED's). And, where Colored (LED's) are utilized, a system as shown in FIG. 3d1 can be used to combine the outputs from a plurality thereof at, at least some of the (S1), (S2), (S3) and (S4) Source locations, (see discussion of FIG. 3d below). Where Colored (LED's) are used, Silicon Photodetectors; instead of more expensive CCD Detectors, can be utilized as the Detector (DET). And since the wavelengths developed are known, said Silicon Photodetectors can be chosen for optimum sensitivity.

FIGS. 1b and 1c show the prefered embodiemnt of the disclosed invention. In the following, other systems which can be utilized as low cost ellipsometers, but which require moving parts are described.

FIGS. 2a–2d show a combined spectroscopic reflectometer/ellipsometer system wherein the source of polychromatic electromagnetic radiation (QTH), and detector (DET) system are common to both, and wherein the spectroscopic ellipsometer system is shown as being provided input and output electromagnetic beam access via fiber optics (F1) and (F2). Shown are near-normal orientation reflectometer electromagnetic beam in (RBI) and reflectometer electromagnetic beam out (RBO), as well as sample system (SS) specific near Brewster condition ellipsometer electromagnetic beam in (EBI) and ellipsometer electromagnetic beam out (EBO). While not shown, it is noted that the source of polychromatic electromagnetic radiation (QTH), and detector (DET) system can be located distal from both the reflectometer and ellipsometer portions of the combined spectroscopic reflectometer/ellipsometer system, with fiber optics being present to interface to the reflectometer portion as well.

In both FIGS. 1a and 2a–2d, there can optionally be other (eg. focusing elements ((FE') (FE')), present on one or both sides of the sample system (SS), as shown in dashed lines. Said other elements appear ellipsometrically indistinguishable with polarization state modifiers, (ie. (A), (B), (C) etc.) during use.

Figure 2A:
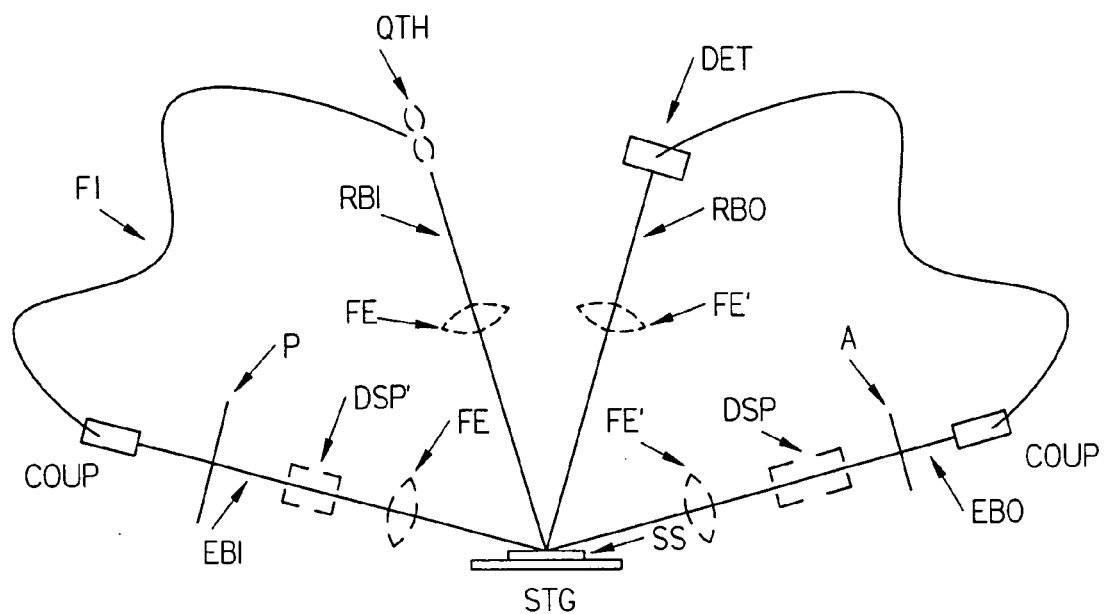
FIGS. 2a–2d show a combined spectroscopic reflectometer/ellipsometer system which can utilize the FIG. 1b soure of electromagnetic radiation.

FIG. 2a shows a combined spectroscopic reflectometer/ellipsometer metrology system wherein the source of polychromatic electromagnetic radiation (QTH), and detector (DET) system are common to both, and wherein the spectroscopic ellipsometer system is shown as being provided input and output electromagnetic beam access via fiber optics (F1) and (F2). Shown are near-normal orientation reflectometer electromagnetic beam in (RBI) and reflectometer electromagnetic beam out (RBO), as well as sample system (SS) specific near Brewster condition ellipsometer electromagnetic beam in (EBI) and ellipsometer electromagnetic beam out (EBO). While not shown, it is noted that the source of polychromatic electromagnetic radiation (QTH), and detector (DET) system can be located distal from both the reflectometer and ellipsometer portions of the combined spectroscopic reflectometer/ellipsometer metrology system, with fiber optics being present to interface to the reflectometer portion as well.

In both FIGS. 1a and 2a, there can optionally be other (eg. focusing elements ((FE') (FE')), present on one or both sides of the sample system (SS), as shown in dashed lines. Said other elements appear ellipsometrically indistinguishable with polarization state modifiers, (ie. (A), (B), (C) etc.) during use.

Figure 2B:
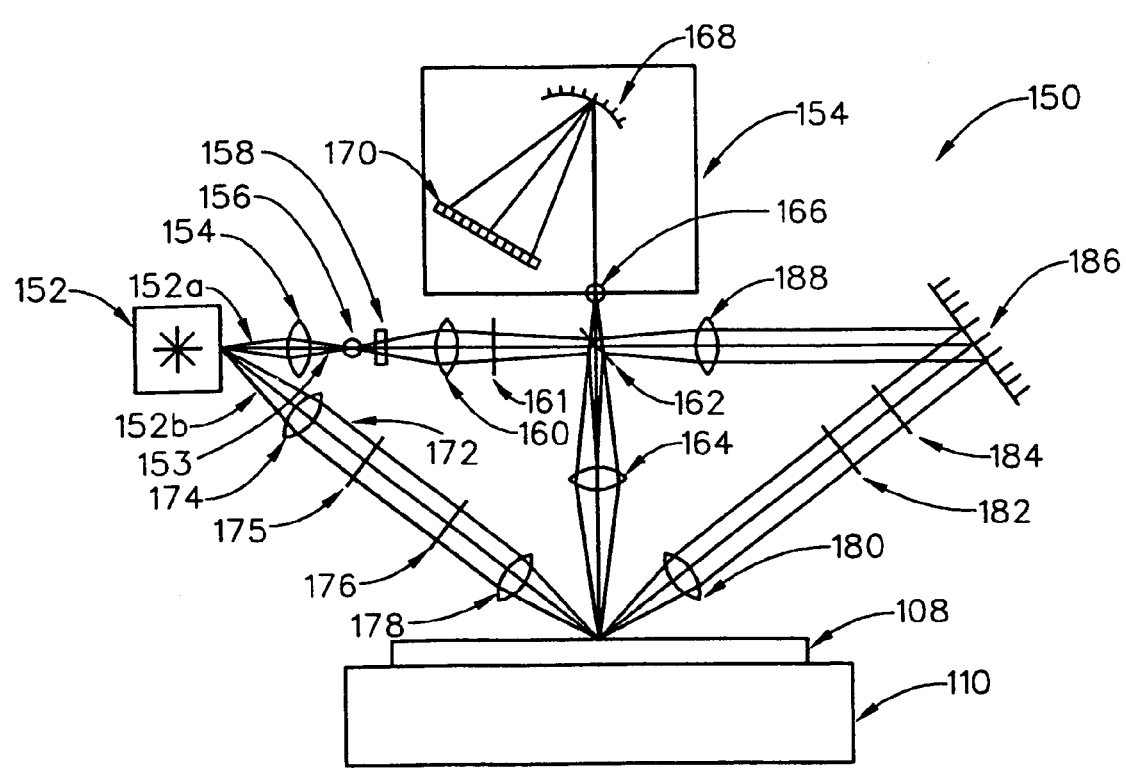
Figure 2C:
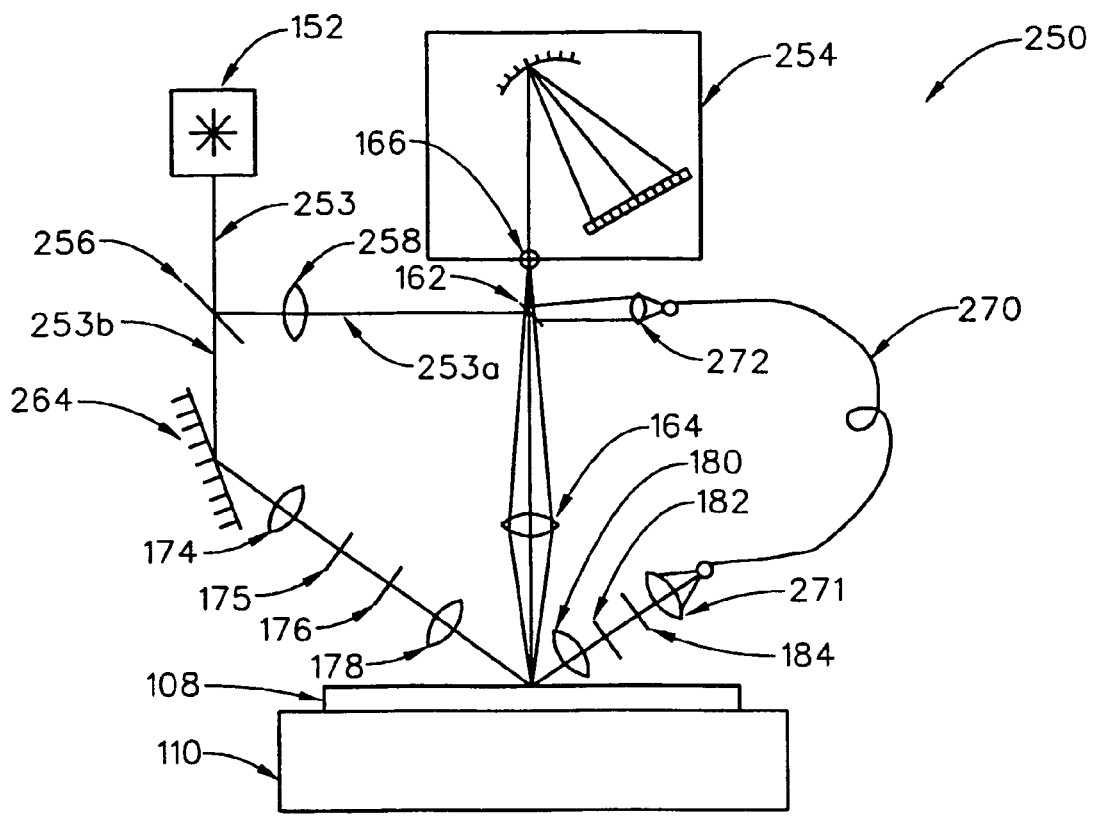
Figure 2D:
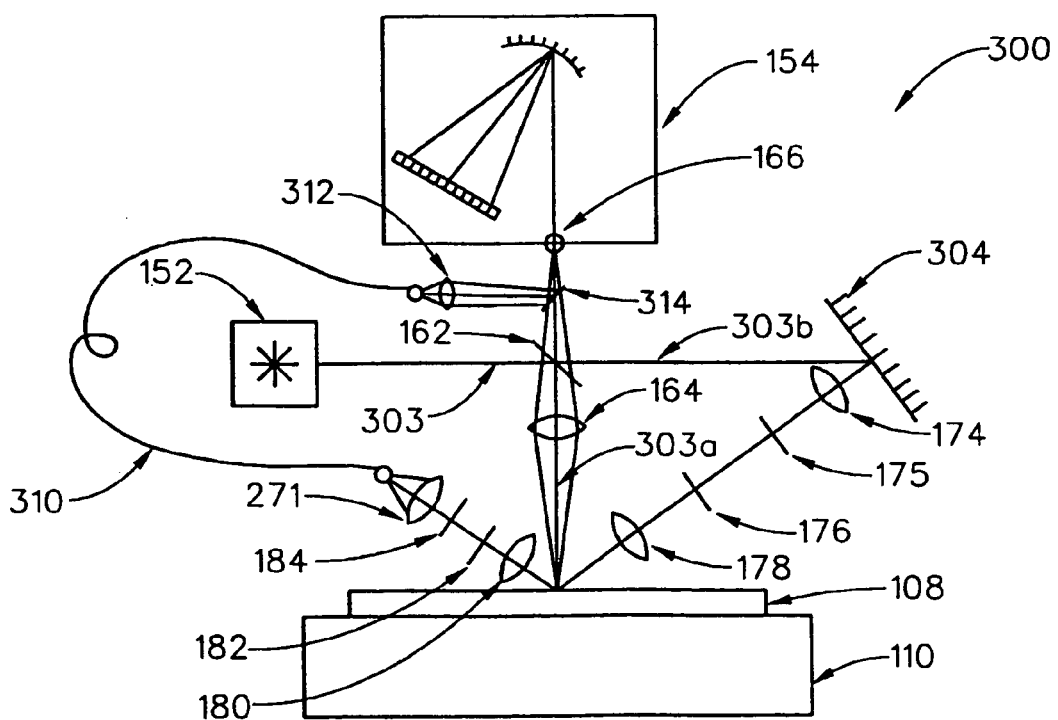
Figure 5:
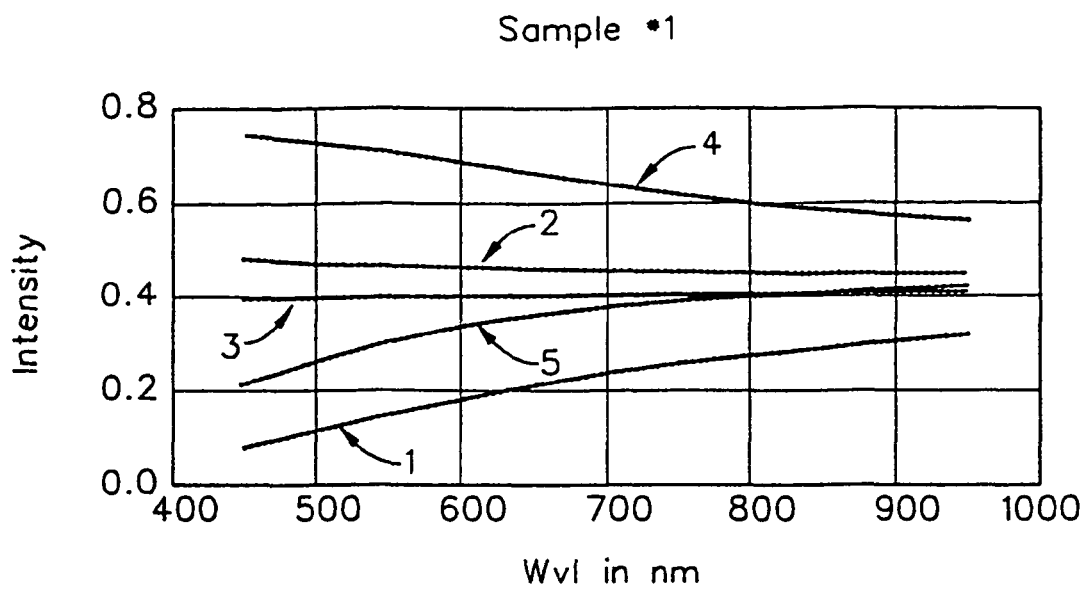
FIGS. 5–11 show Intensity vs. Wavelength for the seven (7) ellipsometrically different samples, obtained by fitting a mathematical model of the samples and a spectroscopic ellipsometer system by regression onto experimentally obtained data obtained at each of five (5) discrete polarization states.
Figure 6:
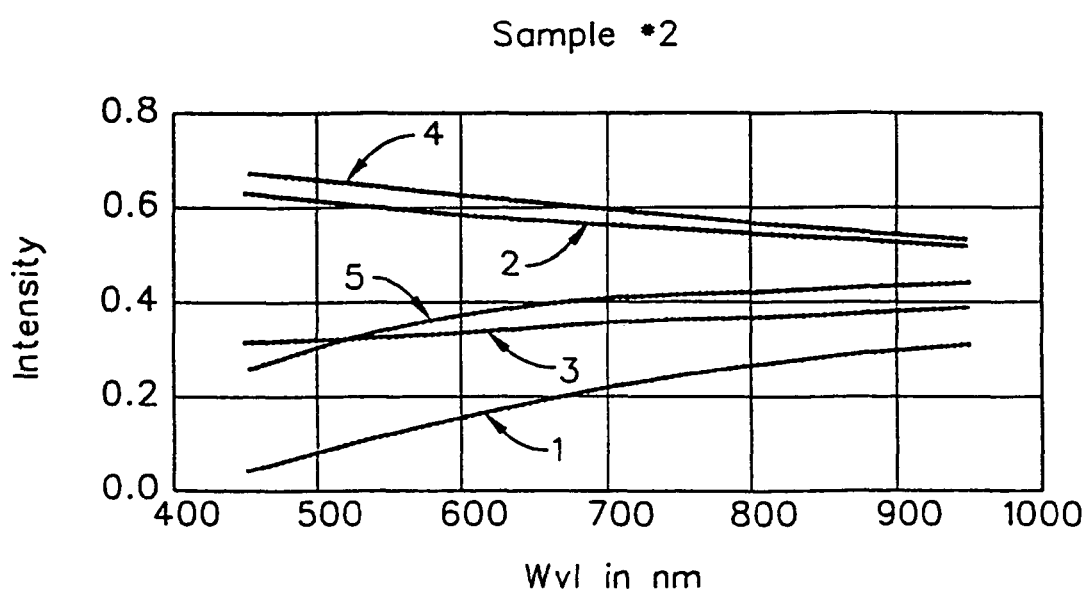
Figure 7:
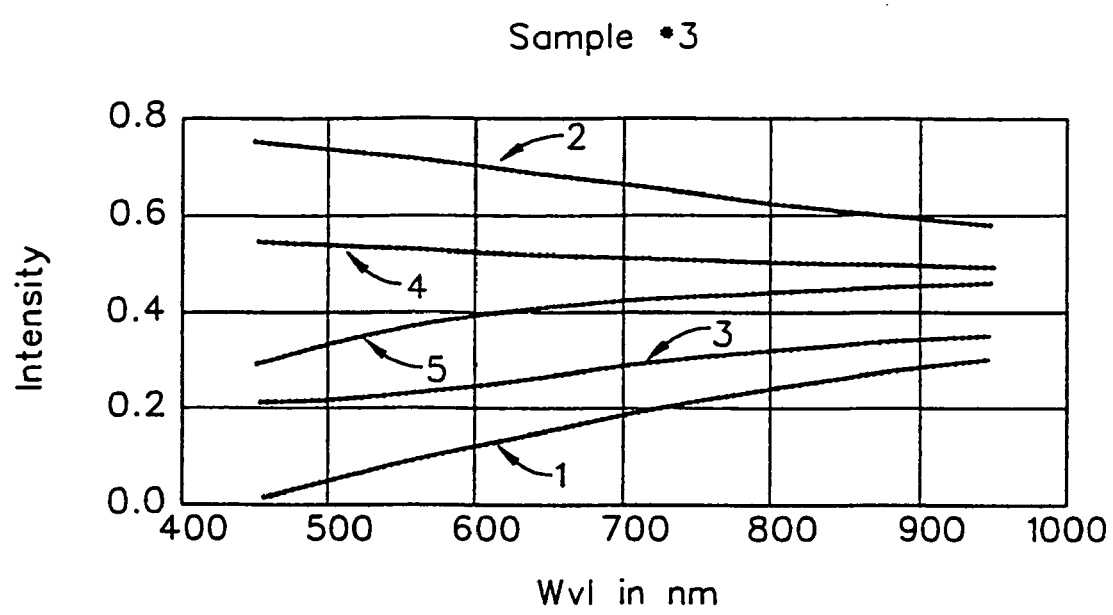
Figure 8:
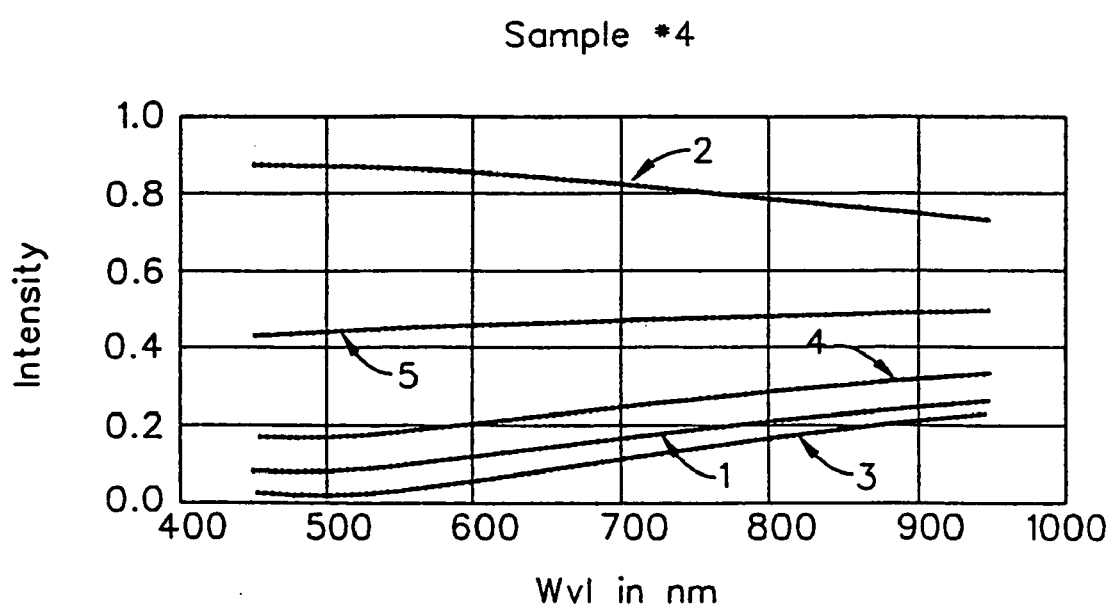
Figure 9:
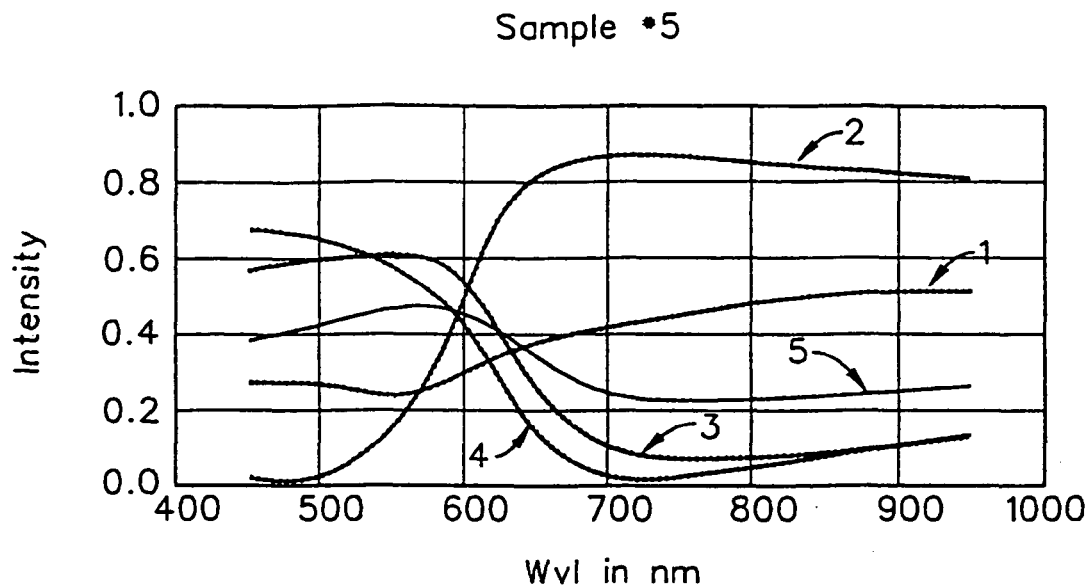
Figure 11:
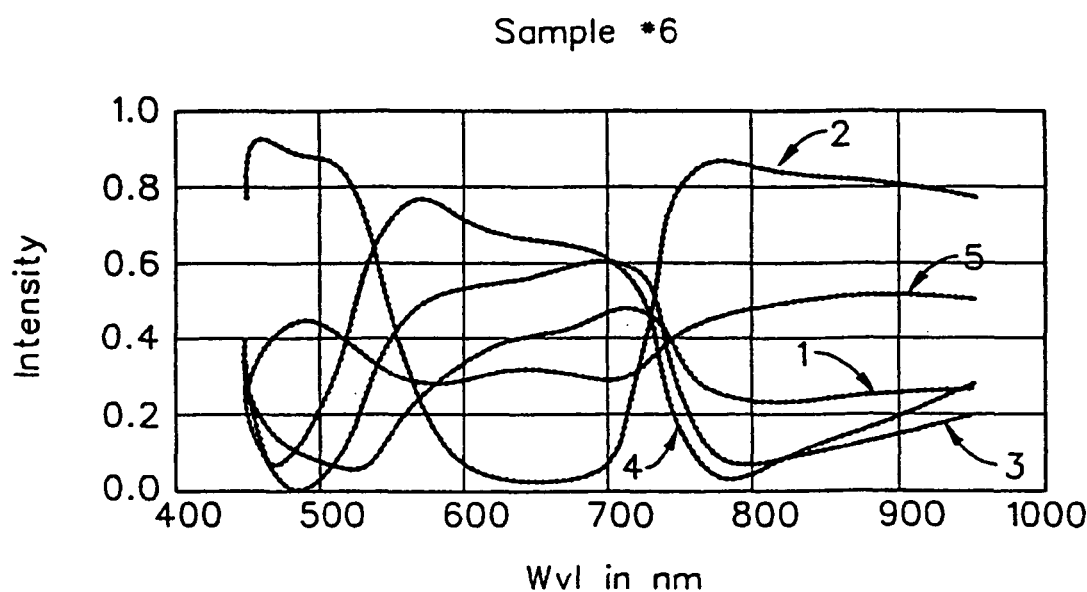
Figure 10:
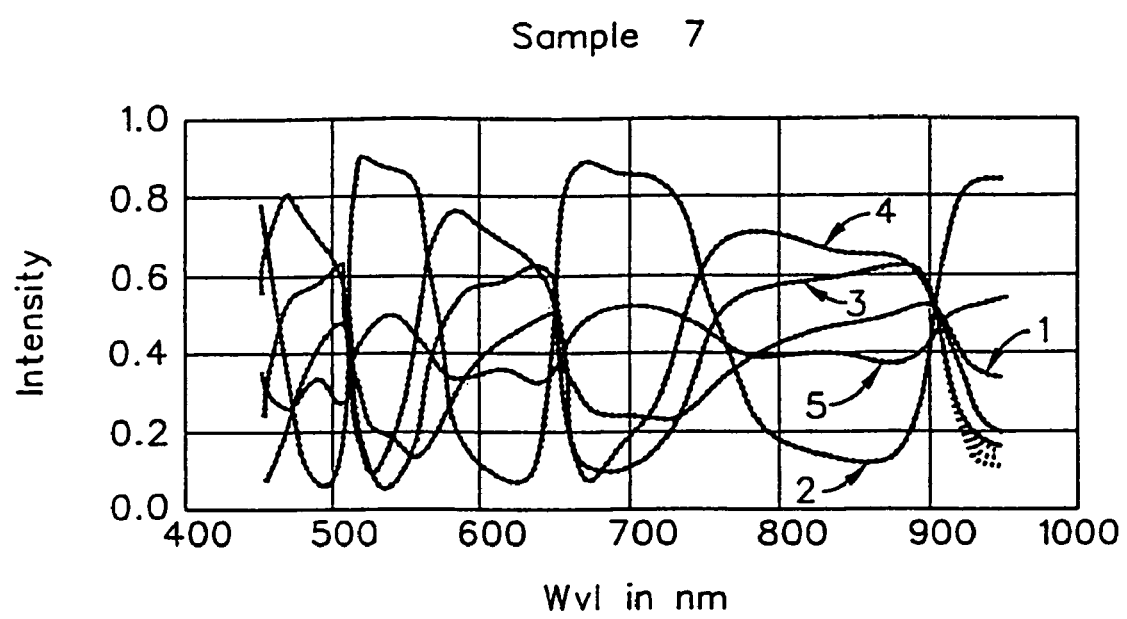

FIGS. 2b–2d show various embodiments of combined present invention spectroscopic reflectometer/ellipsometer systems, described as metrology systems.

Considering first FIG. 2b, there is shown therein a metrology system (150) in which a source of electromagnetic radiation (152) provides two beams of electromagnetic radiation (152a) and (152b). Beam (152b) interacts with optical elements (174), (172), (175), (176) and (178) before reflecting from sample (108). Reflected electromagnetic beam (152b) passes through optical elements (180) and (184), reflects from mirror (186), passes through lens (188), and is focused into entrance slit (166) of detector system (154), by beam splitter (162). Electromagnetic beam (152a) passes through optical elements (154), (156), (158), (160) and (161), then reflects from beam splitter (162) into sample (108) via lens 164, with the beam reflected from the sample (108) then being directed via lens (164) through beam splitter (162) into the detector (154) through entrance slit (166).

FIG. 2c shows that metrology system (250), (which is analogically similar to metrology system 150 shown in FIG. 2b), having a single light source (152) and a single light detector (154). A single beam of electromagnetic radiation (253) is produced by said light source (152) and is split into reflectometer (253a) and an ellipsometer (253b) beams of electromagnetic radiation by beam splitter (256). A series of optics, shown as a single lens (258) for the sake of simplicity, is used to direct light beam (253a) to beam splitter (162) and focus beam (253a) on sample (108) via lens (164). The ellipsometer beam (253b) is redirected with mirror (264) towards the ellipsometric optical elements (174), (175), (176) and (178). Electromagnetic radiation reflected off sample (108) passes through another series of ellipsometric elements (180) (182) and (184) and is entered to fiber optics (270) via lens (271). Electromagnetic radiation (exiting said fiber optics (270) is focused via lens (272) onto beam splitter (162) and directed through entrance slit (166) into detector (254). The fiber optics, it is noted, eliminates the need for electromagnetic beam redirecting means after reflection from the sample (108) and prior to beam splitter (162), thus enabling overall metrology system size reduction.

Focusing now on FIG. 2d, there is shown another embodiment of a present ivnention metrology system (300), (which is similar to metrology system (150) shown in FIG. 2b). Single electromagnetic beam (303) is produced by source (152) and Is split into beams (303a) and (303b) by beam splitter (162). The reflectometer optical path for electromagnetic beam (303a) is similar to that described for the reflectometer electromagnetic beam described in FIG. 2c, but ellipsometer electromagnetic beam (303b) is caused to reflect from mirror (304) and become directed onto sample (108) via optical elements (174), (175), (176) and (178). The electromagnetic beam (303b) which reflects from sample (108) passes through optical elements (180), (182) & (184) and enters fiber optics (310) via lens (271). The electromagnetic beam exiting the fiber optics (310) is, via lens (312), then focused onto entrance slit (166) of detector (254) by beam splitter (314).

With respect to the presently disclosed invention of FIG. 1b, note that the Source (152) can be the Polarization State Generator of FIG. 1b, including the beam combining system of FIG. 3d1.

It should be appreciated that FIGS. 2b–2d show exemplary and not limiting embodiments of combined spectroscopic reflectometer/ellipsometer metrology systems.

FIG. 3a shows a frontal perspective view of a discrete state polarizer (DSP) comprising an essentially circular "wheel" element (WE) with five discrete polarization state modifiers elements (A) (B) (C) (D) and (E) mounted thereupon on the perimeter thereof, such that said and projecting discrete polarization state modifier elements (A) (B) (C) (D) and (E) project perpendicularly to a surface thereof.

FIG. 3b shows a side elevational view of a discrete state polarizer, as in FIG. 3a, oriented so that an electromagnetic beam (EM) passing through one (C) of the five discrete polarization state modifiers (A) (B) (C) (D) and (E) elements. Note that discrete polarizer elements (A) and (B) are located behind discrete polarizer elements (E) and (D) respectively. Also note that if the essentially circular "wheel" element (WE) is caused to rotate about the pivot rod (PR) which projects from a lower surface of said essentially circular "wheel" element, each of the various five discrete polarizer (A) (B) (C) (D) and (E) elements can be rotated into the position in which is shown discrete polarizer element (C).

FIG. 3c shows a front elevational view of a discrete state polarizer with five laterally slideably mounted discrete polarizer (A) (B) (C) (D) and (E) elements mounted on a slider element (SE) which is mounted in a guide providing element (GE) therein. Sliding the slider element (SE) to the right or left serves to position each of the five discrete polarizer (A) (B) (C) (D) and (E) elements in a position at which an electromagnetic beam of radiation can be caused to be present.

In all of the FIGS. 3a–3c embodiments a stepper motor, (not shown), or other functional means, including manual positioning, can be applied to position polarizer elements during use so that an electromagnetic beam passes through a intended discrete polarizer element. In addition, the showing of five discrete polarizer (A) (B) (C) (D) and (E) elements in each of the FIGS. 3a–3c is demonstrative and not meant to indicate a limitation. More or less than five discrete polarizer elements can be present.

Turning now to FIG. 3d1, it is shown that the present invention system source of polychromatic radiation (QTH) as in FIG. 1b can, but not necessarily, be a system as Claimed in U.S. Pat. No. 6,268,917 to Johs, for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a comingled composite of a plurality of input beams, ((IB1) and (IB2)), of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first (SS1) and a second (SS2) source of electromagnetic radiation, ((IB1) and (IB2) respectively); and b. at least one electromagnetic beam combining (BCM) means comprising an uncoated plate, (eg. uncoated fused silica or glass etc. such that transmission characteristics thereof are determined by angle-of-incidence and polarization state of a beam of electromagnetic radiation).

The at least one electromagnetic beam combining means (BCM) is positioned with respect to said first (SS1) and second (SS2) sources of electromagnetic radiation, ((IB1) and (IB2) respectively), such that a beam of electromagnetic radiation (IB1) from said first (SS1) source of electromagnetic radiation passes through said at least one electromagnetic beam combining means (BCM), and such that a beam of electromagnetic radiation (IB2) from said second (SS2) source of electromagnetic radiation reflects from said at least one electromagnetic beam combining means (BCM) and is comingled with said beam of electromagnetic radiation (IB1) from said first source (SS1) of polychromatic electromagnetic radiation which passes through said at least one electromagnetic beam combining means (BCM). The resultant output beam of polychromatic electromagnetic radiation (OB) has a relatively broad and flattened intensity vs. wavelength over a wavelength spectrum, comprising said comingled composite of a plurality of input beams of electromagnetic radiation which individually do not provide such a relatively broad and flattened intensity vs. wavelength over a wavelength spectrum characteristic. It is noted that prefered practice provides that the sources of electromagnetic radiation ((IB1) and (IB2)) each provide a polychromatic output. Also shown in FIG. 3$d$1 are collimating lenses (L1) and (L2) to provide collimated electromagnetic radiation to the electromagnetic beam combining means (BCM), from first (SS1) and a second (SS2) source of polychromatic electromagnetic radiation, ((IB1) and (IB2) respectively).

FIG. 3$d$ further demonstrates an optional third source of, preferably polychromatic, electromagnetic radiation (SS3) and a second electromagnetic beam combining means (BCM'). The second electromagnetic beam combining means (BCM') is positioned with respect to said comingled beam of polychromatic electromagnetic radiation (OB), (which has a relatively broad and flattened intensity vs. wavelength over a wavelength spectrum, comprising wavelengths from sources (SS1) and (SS2), which exits said at least a first electromagnetic beam combining means (BCM)), such that said comingled beam of polychromatic electromagnetic radiation (OB) passes through said second electromagnetic beam combining means (BCM). The second electromagnetic beam combining means (BCM) is positioned with respect to said third source of electromagnetic radiation (SS3) such that a beam of electromagnetic radiation from said third source of electromagnetic radiation (SS3) reflects from said second Further, as described in the Disclosure of the invention Section of this Specification, as the polarizer in the present invention spectroscopic ellipsometer system remains fixed in position during data acquisition, it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between transmission and reflection "S" polarization components is less, as a function of wavelength and electromagnetic beam angle-of-incidence to said beam combining means, compared to that between the "P" components.

FIG. 3$d$2 shows a Beam Chromatic Shifting and Directing Means (ZCM) which comprises a Silicon Substrate (S1) upon the surface of which is present between about 500 and 1500 Angstroms, (nominal 600 or 1200 Angstroms), of Silicon Dioxide (SIO2). FIG. 3$d$3 demonstrates the effect of reflecting the Energy Spectrum provided by a Spectroscopic Source of Electromagnetic Radiation (ZQTH), (see curve (EMI)) corresponding to Beam (EMI) in FIG. 3$d$2, and the corresponding Shifted Energy Spectrum which results from reflection of said input Spectrum.

It is also generally noted that the present invention spectroscopic ellipsometer system can, but not necessarily, utilize Zeiss Diode Array Spectrometer Systems identified by manufacturer numbers in the group: (MMS1 (300–1150 nm); UV/VIS MMS (190–730 nm); UV MMS (190–400 nm); and IR MMS (900–2400 nm)) as Detector System (DET). Said identified Zeiss systems provide a very compact system comprising a multiplicity of Detector Elements and provide focusing via a Focusing Element, Slit, and single concave holographic grating dispersive optics. However, any functional multi-element spectroscopic Detector arrangement is within the scope of the present invention.

FIG. 4$a$ demonstrates a flow of use of the present invnention, electromagnetic beam combining means (BCM) to form a second resultant beam of polychromatic electromagnetic radiation (OB') which is substantially an output beam of polychromatic electromagnetic radiation which has an even more relatively broadened and flattened intensity vs. wavelength over a wavelength spectrum comprising said comingled composite of a plurality of input beams of electromagnetic radiation, (from sources (SS1), (SS2) and (SS3)), which sources (SS1), (SS2) and (SS3) individually do not provide such a relatively broadened and flattened intensity vs. wavelength over a wavelength spectrum characteristic. Note that first or second resultant beam of polychromatic electromagnetic radiation (OB) (OB') in FIG. 3$d$1 can be comprise the source (QTH) in FIG. 1$a$, or be combined (LED) outputs. (It is noted that any of said sources (SS1) (SS2) and (SS3) can be polychromatic electromagnetic radiation sources such as Xenon or Duterium, and Quartz-Halogen lamps, or other suitable source).

A system as shown in FIG. 3$d$1 can also include a pivot(s) (PV) (PV') to allow the beam combining means (BCM) and/or (BCM'), respectively, to be rotated. This can be beneficially applied to allow selection of an optimum angle at which a beam of electromagnetic radiation is caused to reflect therefrom in use. It is noted that the angle at which a beam of electromagnetic radiation approaches a beam combining means affects the percent of an impinging beam which actually reflects therefrom and becomes part of the output beam (OB), and where a beam source positioning can be changed along with pivoting of a beam combining means, this allows optimum combining of transmitted and reflected beams. Also, pivot with two degrees of rotational freedom can be applied to simply effect coincidence of transmitted and reflected beams of electromagnetic radiation which originate from sources which are fixed in location. and FIG. 4$b$ demonstrates the flow of a present invention method of calibration of the spectroscopic ellipsometer portion of the present invention.

FIGS. 5–11 show Intensity vs. Wavelength for the seven (7) ellipsometrically different samples at each of five (5) imposed polarization states. Results shown in FIGS. 5–7 respectively, are for Samples identified as 1, 2, 3, 4, 5, 6, and 7, which respectively have Oxide depths atop thereof of, (in Angstroms), 17.50; 103.0; 193.0; 508.0; 1318.0; 4817.0 and 9961.0.

(Note, the data in FIGS. 5–11 were obtained utilizing a single source of electromagnetic radiation which had a number of polarization state imposed thereupon by means as shown in FIGS. 3$a$–3$c$ being placed into a beam of electromagnetic radiation. Howewver, the same approach demonstrated is directly applicable to the case where a sequence of different polarization states are provided by different discrete sources, each of which provides a different polarization state as demonstrated in FIG. 1*b*).

Figure 12:
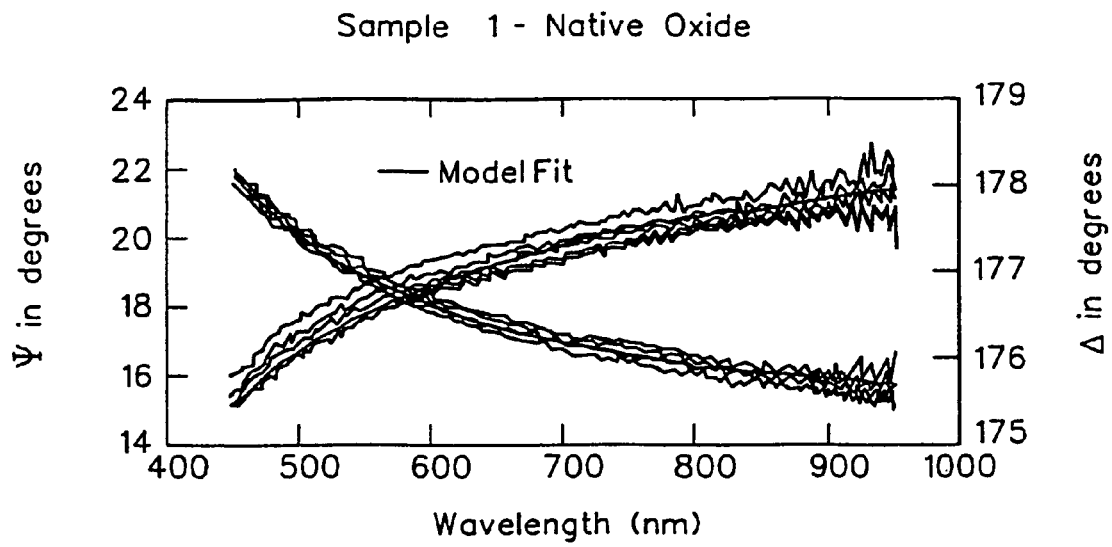
FIGS. 12 & 13 show PSI and DELTA values obtained for samples with thin and thick layers of Oxide thereupon utilizing discrete, rather than continuously varying polarization state data.
Figure 13:
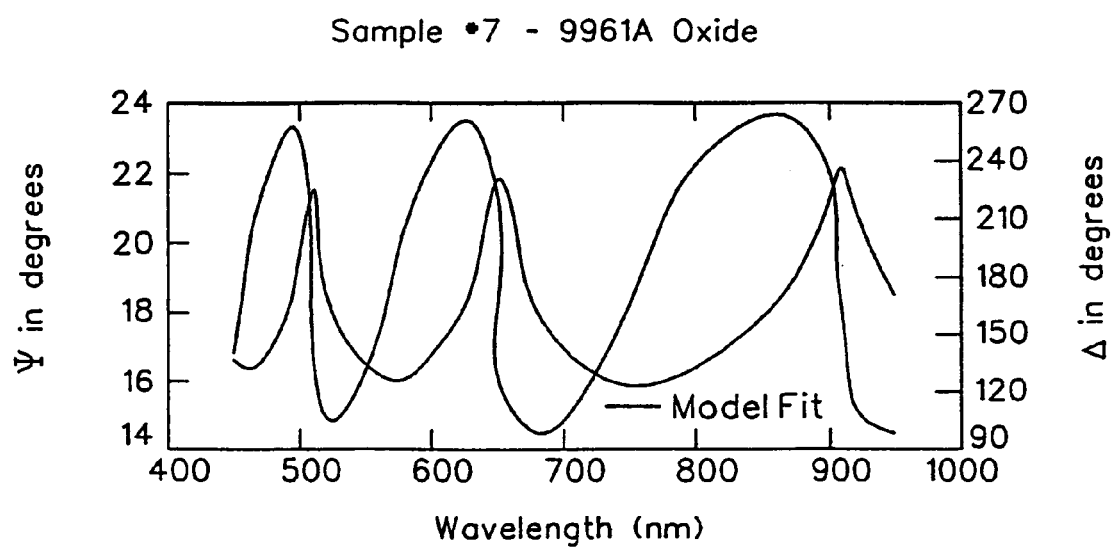

FIGS. 12 & 13 show PSI and DELTA values obtained for samples with thin (native), and thick, (9961 Angstrom), layers of Oxide thereupon. All results were obtained by fitting a mathematical model of the sample system and the spectroscopic ellipsometer system by regression onto experimental data.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A sample system investigation system comprising:
  a) a plurality of electromagnetic radiation sources, each thereof optionally having polarization state setting means functionally associated therewith;
  b) a means for accepting at least two electromagnetic beams which approach along different loci, and providing an electromagnetic beam which exits therefrom along a single locus;
  c) a stage for supporting a sample system;
  d) at least one detector system;

said means for accepting at least two electromagnetic beams which approach along different loci, and providing an electromagnetic beam which exits therefrom along a single locus, being positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system;

said at least one detector system being positioned to intercept a beam which emerges from the sample system on said stage for supporting a sample system after said beam of electromagnetic radiation interacts therewith.

2. A sample system investigation system as in claim 1, in which at least one of said plurality of electromagnetic radiation sources has polarization state setting means functionally associated therewith which changes the phase angle between orthogonal components and/or the magnitude of least one orthogonal component of said electromagnetic beam of radiation.

3. A sample system investigation system as in claim 1, in which at least a first and a second of said plurality of electromagnetic radiation sources each have polarization state setting means functionally associated therewith, the polarization state setting means associated with said first electromagnetic radiation source being set to provide a different polarization state on a beam of electromagnetic radiation emerging therefrom than does the polarization state setting means associated with said second electromagnetic radiation source impose on a beam of electromagnetic radiation emerging from said second electromagnetic radiation source.

4. A sample system investigation system as in claim 1, in which at least one of said plurality of electromagnetic radiation sources provides a beam characterized by a selection from the group consisting of:
  being substantially monochromatic electromagnetic radiation; and
  being polychromatic electomagnetic radiation.

5. A sample system investigation system as in claim 1, in which a focusing lens is present in said beam of electromagnetic radiation which is directed toward a sample system placed on said stage for supporting a sample system.

6. A system as in claim 1 in which at least one of said plurality of electromagnetic radiation sources is a system for for providing an output beam of polychromatic electromagnetic radiation which has a relatively broad and flattened intensity vs. wavelength characteristic over a wavelength spectrum comprising a selection from the group consisting of:
  a. at least a first and a second source of electromagnetic radiation comprising a selection from the group consisting of:
    being substantially monochromatic; and
    being polychromatic; and
  b. at least one electromagnetic beam combining means comprising a plate wherein the transmission characteristics thereof are determined by angle-of-incidence and polarization state of a beam of electromagnetic radiation;

said at least one electromagnetic beam combining means being positioned with respect to said first and second sources of electromagnetic radiation, such that a beam of electromagnetic radiation from said first source of electromagnetic radiation passes through said at least one electromagnetic beam combining means, and such that a beam of electromagnetic radiation from said second source of polychromatic electromagnetic radiation reflects from said at least one electromagnetic beam combining means and is comingled with said beam of electromagnetic radiation from said first source of electromagnetic radiation which passes through said at least one electromagnetic beam combining means, the resultant beam of electromagnetic radiation being substantially an output beam of polychromatic electromagnetic radiation which has a relatively broad and flattened intensity vs. wavelength over a wavelength spectrum, comprising said comingled composite of a plurality of input beams of electromagnetic radiation which individually do not provide such a relatively broad and flattened intensity vs. wavelength over a wavelength spectrum characteristic.

7. A sample system investigation system as in claim 1 in which said first and second sources of electromagnetic radiation comprise light emitting diodes.

8. A sample system investigation system as in claim 1, which further comprises at least one selection from the group consisting of: there is at least one compensator prior to and/or after the stage for supporting a sample system; and the detector system comprises a beam splitting analyzer means and two detector elements.

9. A sample system investigation system as in claim 1, in which the at least a first and a second source of electromagnetic radiation are light emitting diodes and the path length from each of said at least first and second light emitting diodes to said sample are substantially the same.

10. A system as in claim 1 in which at least one of said plurality of electromagnetic radiation sources comprises a system for for providing an output beam of polychromatic electromagnetic radiation which has a relatively broad and flattened intensity vs. wavelength characteristic over a wavelength spectrum comprises a silicon substrate upon a surface of which is present between about 500 and 1500 Angstroms of SiO2, the effect of reflecting a beam of polychromatic radiation therefrom is to de-emphasize intensity in the visual and emphasize intensity in the IR and UV wavelength ranges.

11. A method of analyzing a sample system comprising the steps of:

A) providing a sample system investigation system comprising:
- a) a plurality of electromagnetic radiation sources, each thereof optionally having polarization state setting means functionally associated therewith;
- b) a means for accepting at least two electromagnetic beams which approach along different loci, and providing an electromagnetic beam which exits therefrom along a single locus;
- c) a stage for supporting a sample system;
- d) at least one detector system;
- e) computation means;

said means for accepting at least two electromagnetic beams which approach along different loci, and providing an electromagnetic beam which exits therefrom along a single locus, being positioned with respect to at least two of said plurality of sources of electromagnetic radiation such that a beam of electromagnetic radiation from either thereof, when it is energized, enters thereinto and emerges therefrom along a locus which is directed toward a sample system placed on said stage for supporting a sample system;

said at least one detector system being positioned to intercept a beam which emerges from the sample system on said stage for supporting a sample system after said beam interacts therewith;

- B) energizing one of said sources of electromagnetic radiation and accumulating data from said at least one detector system;
- C) optionally energizing a second of said sources of electromagnetic radiation and accumulating data from said at least one detector system;
- D) optionally energizing a third of said sources of electromagnetic radiation and accumulating data from said at least one detector system;
- E) optionally energizing a fourth of said sources of electromagnetic radiation and accumulating data from said at least one detector system;
- F) applying said computation means to analyze said sample system utilizing said accumulated data.

12. A method of analyzing a sample system as in claim 11, in which the step of providing a sample system investigation system involves providing a sample system investigation system characterized by a selection from the group consisting of:

- none of said plurality of electromagnetic radiation sources has polarization state setting means functionally associated therewith;
- at least one of said plurality of electromagnetic radiation sources has polarization state setting means functionally associated therewith;
- at least one of said plurality of electromagnetic radiation sources provides a beam of substantially monochromatic electomagnetic radiation;
- at least one of said plurality of electromagnetic radiation sources provides a beam of polychromatic electomagnetic radiation;
- at least a first and a second of said plurality of electromagnetic radiation sources each have polarization state setting means functionally associated therewith, the polarization state setting means associated with said first electromagnetic radiation source being set to provide a different polarization state on a beam of electromagnetic radiation emerging therefrom than does the polarization state setting means associated with said second electromagnetic radiation source impose on a beam of electromagnetic radiation emerging from said second electromagnetic radiation source.

13. A method of analyzing a sample system as in claim 11, in which at least a first and a second of said plurality of electromagnetic radiation sources each have polarization state setting means functionally associated therewith, the polarization state setting means associated with said first electromagnetic radiation source being set to provide a different polarization state on a beam of electromagnetic radiation emerging therefrom than does the polarization state setting means associated with said second electromagnetic radiation source impose on a beam of electromagnetic radiation emerging from said second electromagnetic radiation source, and in which said at least first and second of said plurality of electromagnetic radiation sources are sequentially energized in steps B) and (C).

14. A sample system investigation system comprising:
- a) at least a first and a second source of electromagnetic radiation, each thereof having polarization state setting means functionally associated therewith;
- b) at least a first electromagnetic beam combining means;
- c) a stage for supporting a sample system;
- d) analyzer means;
- e) at least one detector system;

said at least a first electromagnetic beam combining means being positioned with respect to first and second sources of electromagnetic radiation such that a polarized beam of electromagnetic radiation from said first source of electromagnetic radiation, when it is energized, passes through said at least a first electromagnetic beam combining means, and such that a polarized beam of electromagnetic radiation from said second source of electromagnetic radiation, when it is energized, reflects from said at least a first electromagnetic beam combining means;

a beam of electromagnetic radiation exiting said first electromagnetic beam combining means along a locus which is directed toward a sample system placed on said stage for supporting a sample system;

said at least one detector system comprising said analyzer means and being positioned to intercept a beam which emerges from the sample system on said stage for supporting a sample system after interaction therewith.

15. A sample system investigation system as in claim 14, which further comprsises:
- f) a third and a fourth source of electromagnetic radiation, each thereof having polarization state setting means functionally associated therewith;
- g) a second electromagnetic beam combining means; and
- h) a third electromagnetic beam combining means;

said third electromagnetic beam combining means being positioned such that said beam of electromagnetic beam exiting said first electromagnetic beam combining means along a locus which is directed toward a sample system placed on said stage for supporting a sample system, passes therethrough before proceeding toward said sample system;

said second electromagnetic beam combining means being positioned with respect to said third and fourth sources of electromagnetic radiation such that a polarized beam of electromagnetic radiation from said third source of electromagnetic radiation, when it is energized, passes through said second electromagnetic beam combining means, and such that a polarized beam of electromagnetic radiation from said fourth source of electromagnetic radiation, when it is energized, reflects from said second electromagnetic beam combining means;

a beam of electromagnetic radiation exiting said second electromagnetic beam combining means along a locus which is directed toward said third electromagnetic beam combining means, reflects off thereof and proceed toward said sample system;

said at least one detector system comprising said analyzer means and being positioned to intercept a beam which emerges from the sample system on said stage for supporting a sample system after interaction therewith.

16. A sample system investigation system as in claim 15 in which the polarization state setting means functionally associated with said first and second and third and fourth sources of electromagnetic radiation are at azimuthal orientations offset from one another.

17. A sample system investigation system as in claim 15 in which the polarizer means functionally associated with said first and second and third and fourth sources of electromagnetic radiation are at azimuthal orientations offset 45 degrees from one another.

18. A sample system investigation system as in claim 15 in which said at least one detector system comprises a polarization state dependent beam splitter and two detectors, which each receive a beam emerging from said beam splitter.

19. A sample system investigation system as in claim 14 in which the polarization state setting means functionally associated with said first and second sources of electromagnetic radiation are at azimuthal orientations offset from one another.

20. A sample system investigation system as in claim 14 in which the polarization state setting means functionally associated with said first and second sources of electromagnetic radiation are at azimuthal orientations offset 45 degrees from one another.

21. A sample system investigation system as in claim 14 in which said first, second, third and fourth sources of electromagnetic radiation comprise light emitting diodes.

22. A sample system investigation system as in claim 14 in which said at least one detector system comprises a polarization state dependent beam splitter and two detectors, which each receive a beam emerging from said beam splitter.

23. A sample system investigation system as in claim 14, which further comprises at least one selection from the group consisting of: there is at least one compensator prior to and/or after the stage for supporting a sample system; and the detector system comprises a beam splitting analyzer means and two detector elements.

24. A sample system investigation system as in claim 14 in which the at least a first and a second source of electromagnetic radiation are light emitting diodes and the path length from each of said at least first and second light emitting diodes to said sample are substantially the same.

25. A method of analyzing a sample system comprising the steps of:
A) providing a sample system investigation system comprising:
   a) at least a first and a second source of electromagnetic radiation, each thereof having polarization state setting means functionally associated therewith, said polarization state setting means functionally associated with said first and said second sources of electromagnetic radiation being at azimuthal orientations offset from one another;
   b) first electromagnetic beam combining means;
   c) a stage for supporting a sample system;
   d) analyzer means;
   e) at least one detector system;
   f) computational means;

said first electromagnetic beam combining means being positioned with respect to first and second sources of electromagnetic radiation such that a polarized beam of electromagnetic radiation from said first source of electromagnetic radiation, when it is energized, passes through said first electromagnetic beam combining means, and such that a polarized beam of electromagnetic radiation from said second source of electromagnetic radiation, when it is energized, reflects from said at least a first electromagnetic beam combining means;

a beam of electromagnetic radiation exiting said first electromagnetic beam combining means being along a locus which is directed toward a sample system placed on said stage for supporting a sample system such that it interacts with said sample system and proceeds into said analyzer means;

said at least one detector system comprising said analyzer means and being positioned to intercept a beam which emerges from the sample system on said stage for supporting a sample system after interaction therewith;

then in either order practicing the following steps B and C:
   B) energizing said first source of electromagnetic radiation and accumulating data from said at least one detector system; and
   C) energizing said second source of electromagnetic radiation and accumulating data from said at least one detector system;

and then practicing step D);
   D) applying said computation means to analyze said sample system utilizing said accumulated data.

26. A method of analyzing a sample system as in claim 25 in which the step of providing at least a first and a second source of electromagnetic radiation involves providing light emitting diodes which are positioned such that the path length from each of said at least first and second light emitting diodes to said sample are substantially the same.

27. A method of analyzing a sample system comprising the steps of:
A) providing a sample system investigation system comprising:
   a) first, second, third and fourth sources of electromagnetic radiation, each thereof having polarization state setting means functionally associated therewith, said polarization state setting means functionally associated with said first, second, third and fourth sources of electromagnetic radiation being at orientations offset from one another;
   b) first, second and third electromagnetic beam combining means;
   c) a stage for supporting a sample system;
   d) analyzer means;
   e) at least one detector system;
   f) a computation means;

said first electromagnetic beam combining means being positioned with respect to first and second sources of electromagnetic radiation such that a polarized beam of electromagnetic radiation from said first source of electromagnetic radiation, when it is energized, passes through said at least said first electromagnetic beam combining means, and such that a polarized beam of electromagnetic radiation from said second source of electromagnetic radiation, when it is energized, reflects from said at least a first electromagnetic beam combining means;

said second electromagnetic beam combining means being positioned with respect to said third and fourth sources of electromagnetic radiation such that a polarized beam of electromagnetic radiation from said third source of electromagnetic radiation, when it is energized, passes through said second electromagnetic beam combining means, and such that a polarized beam of electromagnetic radiation from said fourth source of electromagnetic radiation, when it is energized, reflects from said second electromagnetic beam combining means;

said third electromagnetic beam combining means being positioned such that said beam of electromagnetic beam exiting said first electromagnetic beam combining means passes therethrough and proceeds toward said sample system and such that such that said beam of electromagnetic beam exiting said second electromagnetic beam combining means reflects therefrom and proceeds toward said sample system;

said at least one detector system comprising said analyzer means and being positioned to intercept a beam which emerges from the sample system on said stage for supporting a sample system after interaction therewith;

then in any functional order practicing at least two steps selected from the group consisting of:

B) energizing said first source of electromagnetic radiation and accumulating data from said at least one detector system;

C) energizing said second source of electromagnetic radiation and accumulating data from said at least one detector system;

D) energizing said third source of electromagnetic radiation and accumulating data from said at least one detector system;

E) energizing said fourth source of electromagnetic radiation and accumulating data from said at least one detector system; and F) applying said computation means to analyze said sample system utilizing said accumulated data.

28. A method of analyzing a sample system as in claim 27 in which the step of providing at least a first and a second source of electromagnetic radiation involves providing light emitting diodes.

* * * * *